United States Patent
Westlund High et al.

(10) Patent No.: US 12,145,991 B2
(45) Date of Patent: Nov. 19, 2024

(54) THERAPEUTIC ANTIBODY FRAGMENTS, METHODS OF MAKING, AND METHODS OF USE

(71) Applicants: UNM Rainforest Innovations, Albuquerque, NM (US); LOYOLA UNIVERSITY OF CHICAGO, Maywood, IL (US)

(72) Inventors: Karin Westlund High, Albuquerque, NM (US); Ravi Venkata Durvasula, Albuquerque, NM (US); Adinarayana Kunamneni, Albuquerque, NM (US)

(73) Assignees: UNM Rainforest Innovations, Albuquerque, NM (US); Loyola University of Chicago, Maywood, IL (US)

( * ) Notice: Subject to any disclaimer, the term of this patent is extended or adjusted under 35 U.S.C. 154(b) by 727 days.

(21) Appl. No.: 17/284,208

(22) PCT Filed: Nov. 1, 2019

(86) PCT No.: PCT/US2019/059366
§ 371 (c)(1),
(2) Date: Apr. 9, 2021

(87) PCT Pub. No.: WO2020/092883
PCT Pub. Date: May 7, 2020

(65) Prior Publication Data
US 2021/0340265 A1    Nov. 4, 2021

Related U.S. Application Data

(60) Provisional application No. 62/890,879, filed on Aug. 23, 2019, provisional application No. 62/769,181, filed on Nov. 19, 2018, provisional application No. 62/755,054, filed on Nov. 2, 2018.

(51) Int. Cl.
*C07K 16/28* (2006.01)
*A61K 39/00* (2006.01)
*A61P 25/02* (2006.01)
*A61P 29/02* (2006.01)

(52) U.S. Cl.
CPC ........ *C07K 16/2869* (2013.01); *A61P 25/02* (2018.01); *A61P 29/02* (2018.01); *A61K 2039/505* (2013.01); *C07K 2317/622* (2013.01)

(58) Field of Classification Search
None
See application file for complete search history.

(56) References Cited

U.S. PATENT DOCUMENTS

| | | |
|---|---|---|
| 8,877,898 B2 | 11/2014 | Markiv et al. |
| 2004/0001842 A1 | 1/2004 | Michaeli et al. |
| 2006/0134109 A1* | 6/2006 | Gaitanaris ............... A61P 11/00 435/325 |
| 2016/0207991 A1* | 7/2016 | Bloom ................... A61K 45/06 |
| 2017/0166634 A1 | 6/2017 | Williams et al. |
| 2022/0298238 A1 | 9/2022 | High et al. |

FOREIGN PATENT DOCUMENTS

| | | |
|---|---|---|
| CN | 115244082 A | 10/2022 |
| JP | 2017515473 A | 6/2017 |
| WO | WO-2016034968 A1 | 3/2016 |
| WO | WO-2020092883 A1 | 5/2020 |
| WO | WO-2021041194 A1 | 3/2021 |

OTHER PUBLICATIONS

Tohidkia et al (Selection of Potential Therapeutic Human Single-Chain Fv Antibodies against Cholecystokinin-B/Gastrin Receptor by Phage Display Technology, BioDrugs (2013) 27:55-67), (Year: 2013).*
Yin et al (Transcriptomic and behavioral characterization of a mouse model of burn pain identify the cholecystokinin 2 receptor as an analgesic target, Mol Pain, vol. 12: 1-13, 2016) , (Year: 2016).*
Bertoglio et al (Involvement of dorsolateral periaqueductal gray cholecystokinin-2 receptors in the regulation of a panic-related behavior in rats, Brain Res. Oct. 12, 2005;1059(1):46-51), (Year: 2005).*
GeneCards: CCKBR Gene, (Retrieved Feb. 2024) (Year: 2024).*
Campbell et al (A monomeric red fluorescent protein, A monomeric red fluorescent protein. Proc Natl Acad Sci U S A. Jun. 11, 2002; 99(12):7877-8) (Year: 2002).*
Malhotra (Methods in Enzymology, Chapter 16: Tagging for Protein Expression, vol. 463, 2009). (Year: 2009).*
"International Application Serial No. PCT/US2019/059366, International Preliminary Report on Patentability mailed Apr. 27, 2021", 6 pgs.
"International Application Serial No. PCT/US2019/059366, International Search Report mailed Feb. 13, 2020", 4 pgs.
"International Application Serial No. PCT/US2019/059366, Written Opinion mailed Feb. 13, 2020", 5 pgs.
"International Application Serial No. PCT/US2020/047360, International Search Report mailed Nov. 19, 2020", 2 pgs.
"International Application Serial No. PCT/US2020/047360, Written Opinion mailed Nov. 19, 2020", 3 pgs.
Bertoglio, Leandro Jose, "Involvement of dorsolateral periaqueductal gray cholecystokinin-2 receptors in the regulation of a panic-related behavior in rats", Brain Res. 1059, (Oct. 12, 2005), 46-51.

(Continued)

*Primary Examiner* — Laura B Goddard
*Assistant Examiner* — Sarah A Alsomairy
(74) *Attorney, Agent, or Firm* — Schwegman Lundberg & Woessner, P.A.

(57) ABSTRACT

A pharmaceutical composition generally includes a therapeutic antibody, or fragment thereof, and a pharmaceutically acceptable carrier. The therapeutic antibody specifically binds to a target peptide that mediates pain in a subject. The composition may be administered to a subject experiencing pain to at least partially alleviate the pain.

13 Claims, 11 Drawing Sheets
Specification includes a Sequence Listing.

(56) References Cited

OTHER PUBLICATIONS

Ghilardi, Joseph R, et al., "Trigeminal and Dorsal Root Ganglion Neurons Express CCK Receptor Binding Sites in the Rat, Rabbit, and Monkey: Possible Site of Opiate-CCK Analgesic Interactions", Journal of Neuroscience 12(12), (Dec. 1992), 4854-4866.

Tohidkia, Mohammad R, et al., "Selection of Potential Therapeutic Human Single-Chain Fv Antibodies against Cholecystokinin-B/Gastrin Receptor by Phage Display Technology", BioDrugs 27, (Feb. 2013), 55-67.

Yin, Kathleen, et al., "Transcriptomic and behavioural characterisation of a mouse model of burn pain identify the cholecystokinin 2 receptor as an analgesic target", Mol Pain 12, (Aug. 28, 2016), 1-13.

"European Application Serial No. 20856069.8, Response Filed Oct. 25, 2022 to Communication Pursuant to Rules 161(2) and 162 EPC mailed Jun. 1, 2022", 3 pgs.

"International Application Serial No. PCT/US2020/047360, International Preliminary Report on Patentability mailed Mar. 3, 2022", 5 pgs.

"European Application Serial No. 20856069.8, Extended European Search Report mailed Aug. 9, 2023", 6 pgs.

Bennett, Gary, et al., "A peripheral mononeuropathy in rat that produces disorders of pain sensation like those seen in man", Pain, 33, (1988), 87-107.

Decosterd, Isabelle, et al., "Spared nerve injury: an animal model of persistent peripheral neuropathic pain", Pain, 87, (2000), 149-158.

Kunamneni, A, et al., "Generating highly potent and efficacious antibodies to the cholecystokinin B (CCK-B) receptor by ribosome display for the treatment of neuropathic pain (abstract)", Pharmacology, vol. 33, Issue S1. This abstract is from the Experimental Biology 2019 Meeting. There is no full text article associated with this abstract published in The FASEB Journal., (Apr. 2019), IB31-IB31.

Kunamneni, A, et al., "Generation and Selection of a Panel of Pan-Filovirus Single-Chain Antibodies using Cell-Free Ribosome Display", Am. J. Trop. Med. Hyg., 101(1), (2019), 198-206.

Kunamneni, A, et al., "Ribosome display for the rapid generation of high-affinity Zika-neutralizing single-chain antibodies", PLoS ONE 13(11);e205743, (2018), 1-13.

Lyons, Danielle, et al., "Combination Drug Therapy of Pioglitazone and D-cycloserine Attenuates Chronic Orofacial Neuropathic Pain and Anxiety by Improving Mitochondrial Function Following Trigeminal Nerve Injury (abstract)", Clin J Pain, 34(2), pp. 168-177, (Feb. 2018), 2 pgs.

Ma, F, et al., "Dysregulated TNFa Promotes Cytokine Proteome Profile Increases and Bilateral Orofacial Hypersensitivity", Neuroscience, 300, pp. 493-507, (2015), 29 pgs.

Mamet, Julien, et al., "Single intrathecal administration of the transcription factor decoy AYX1 prevents acute and chronic pain after incisional, inflammatory, or neuropathic injury (abstract)", Pain 155(2), pp. 322-333, (Feb. 2014), 1 pg.

Shields, Shannon, et al., "Spared nerve injury model of neuropathic pain in the mouse: a behavioral and anatomic analysis (abstract)", J Pain, 4(8), pp. 465-470, (Oct. 2003), 1 pg.

Williams, Wendy, et al., "Antibodies binding the head domain of P2X4 inhibit channel function and reverse neuropathic pain", Pain, vol. 160, No. 9, (2019), 1989-2003.

"European Application Serial No. 20856069.8, Response Filed Feb. 29, 2024 to Extended European Search Report mailed Aug. 9, 2023", 8 pgs.

"Japanese Application Serial No. 2022-512748, Notification of Reasons for Refusal mailed Jul. 23, 2024", w/ English translation, 8 pgs.

\* cited by examiner

CCK-B specific scFv

A. Light/Dark Anxiety Test

B. Sucrose Splash Depression Test (A)  (B)  (C)  (D)  (E)

(A)

(B)

THERAPEUTIC ANTIBODY FRAGMENTS, METHODS OF MAKING, AND METHODS OF USE

CROSS-REFERENCE TO RELATED APPLICATION

This application is the § 371 U.S. National Stage of International Application No. PCT/US2019/059366, filed Nov. 1, 2019, which claims the benefit of U.S. Provisional Patent Application No. 62/755,054, filed Nov. 2, 2018, U.S. Provisional Patent Application No. 62/769,181, filed Nov. 19, 2018, and U.S. Provisional Patent Application No. 62/890,879, filed Aug. 23, 2019, each of which is incorporated herein by reference in its entirety.

SEQUENCE LISTING

This application contains a Sequence Listing electronically submitted via EFS-Web to the United States Patent and Trademark Office as an ASCII text file entitled "310-000139WO01_SequenceListing_ST25.txt" having a size of 28 kilobytes and created on Dec. 17, 2019. The information contained in the Sequence Listing is incorporated by reference herein.

GOVERNMENT FUNDING

This invention was made with government support under DE028096 awarded by the National Institutes of Health. The government has certain rights in the invention.

SUMMARY

This disclosure describes, in one aspect, a pharmaceutical composition that generally includes a therapeutic antibody, or fragment thereof, and a pharmaceutically acceptable carrier. The therapeutic antibody specifically binds to a target peptide that mediates pain in a subject.

In some embodiments, the target is an extracellular binding portion of cholecystokinin B (CCK-B) receptor.

In some embodiments, the antibody is an scFv.

In some embodiments, the antibody includes at least one of SEQ ID NOs:3-10. In some of these embodiments, the antibody includes at least one of SEQ ID NOs:3-5.

In some embodiments, the antibody includes a fluorescent tag.

In some embodiments, the antibody includes an affinity tag.

In some embodiments, the composition relieves acute orofacial pain.

In some embodiments, the composition relieves chronic orofacial pain.

In some embodiments, the composition reduces anxiety-related behaviors.

In another aspect, this disclosure describes a method for relieving pain. The method generally includes administering to a subject experiencing pain any embodiment of the composition summarized above in an amount effective to alleviate the pain.

In some embodiments, the pain is orofacial pain.

In some embodiments, the orofacial pain is neuropathic.

The above summary is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

BRIEF DESCRIPTION OF THE FIGURES

The patent or application file contains at least one drawing executed in color. Copies of this patent or patent application publication with color drawing(s) will be provided by the Office upon request and payment of the necessary fee.

Figure 7:
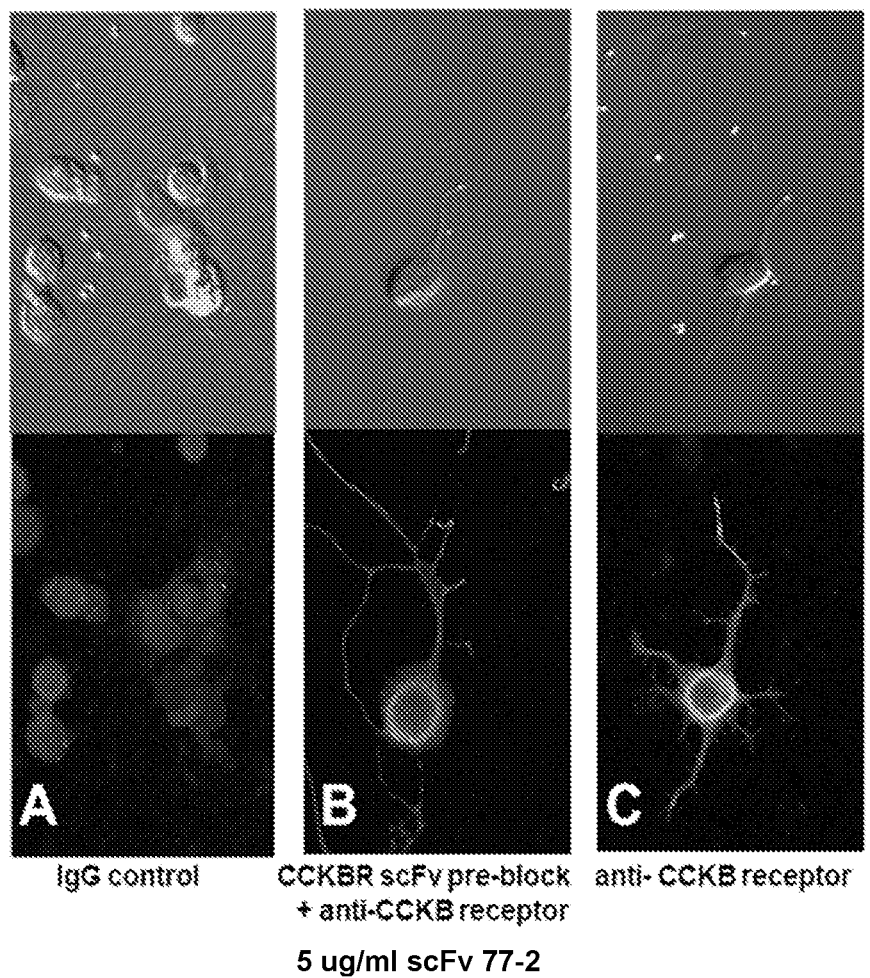
Figure 7:
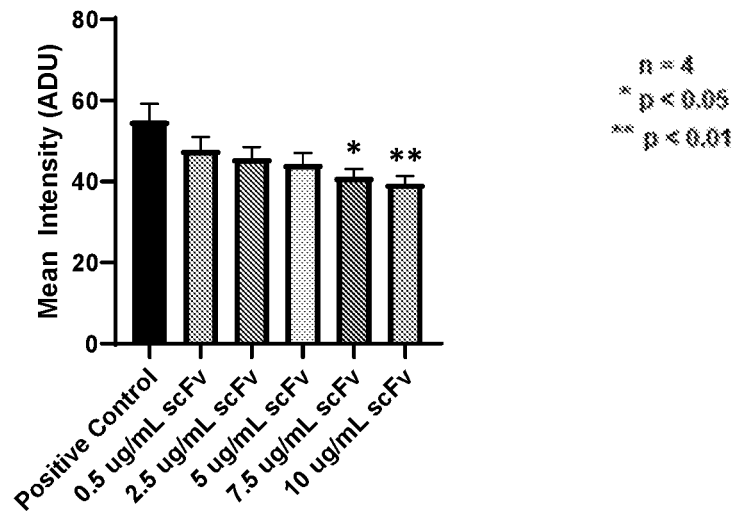

FIG. 7. Adsorption block immunostaining of CCK-B receptor in trigeminal ganglia (TG) with and without pre-staining block with scFv 77-2. (A) Negative control incubated with secondary IgG only. (B) Trigeminal ganglia blocked (24 hours) with 77-2 scFv before immunostaining for CCK-B receptor with a commercial antibody. (C) Trigeminal ganglia immunostained for CCK-B receptor peptide at the membrane. (40×). Top panel of (A), (B), and (C) show phase contrast images of the same cells. (D) Dose sequential block was determined. (40×).

Figure 8:
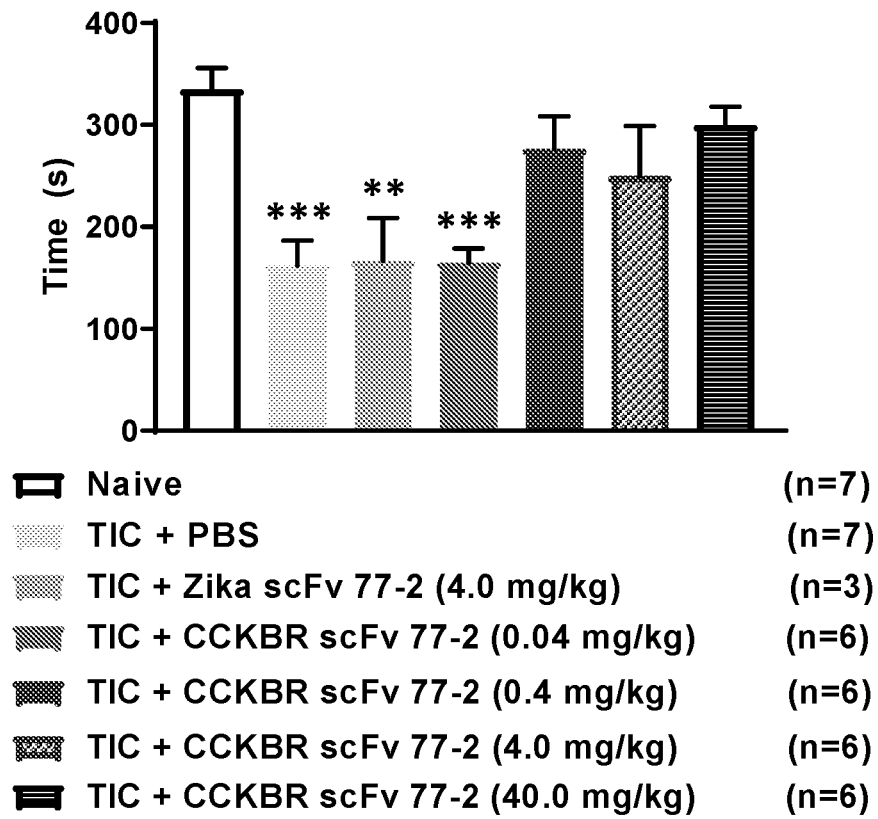

FIG. 8. Anxiety test. Efficacy for anxiety reduction. In the Trigeminal Inflammatory Compression (TIC) model, the 77-2 scFv was efficacious in reducing anxiety at the three highest doses, but not at the two lowest doses or with an alternative neutral scFv (Zika). *p<0.05, p<0.01, * p<0.001.

Figure 9:
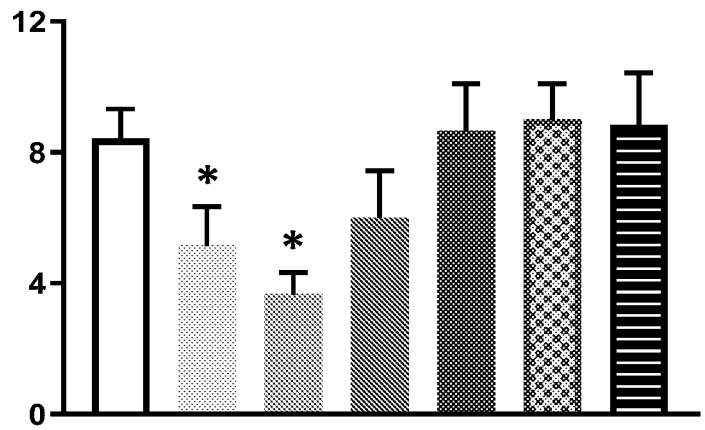

FIG. 9. Depression test. Efficacy for reduction of depression behavior. The sucrose splash test for depression indicated the 77-2 scFv antibody was efficacious in reducing depression at the three highest doses—i.e., increasing grooming time—for the mice with neuropathic pain (TIC model) (week 8). Grooming time after sucrose splash to the rump did not change with the lowest scFv dose or with an alternate neutral scFv (Zika). *p<0.05 compared to vehicle treated control mice with no neuropathic pain.

Figure 10:
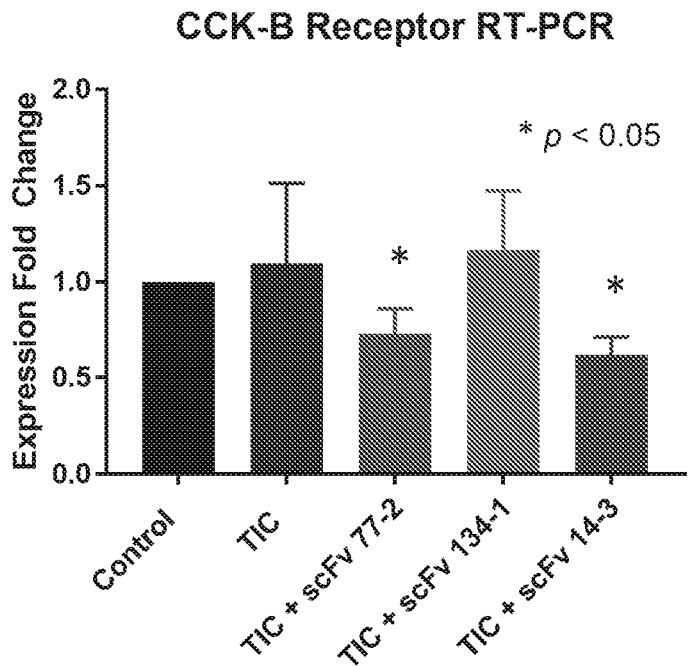

FIG. 10. Trigeminal ganglia neuron RT-PCR. TIC neuropathic pain model (TIC) produced a two-fold RNA increase for CCK-B receptor compared to the control (Control). Treatment with scFv antibodies 77-2 and 14-3, which are effective for reduction of pain-related behaviors, reduced CCK-B receptor RNA similar to that of naïve mice (n=2-4; t-tests; *p<0.05).

Figure 11:
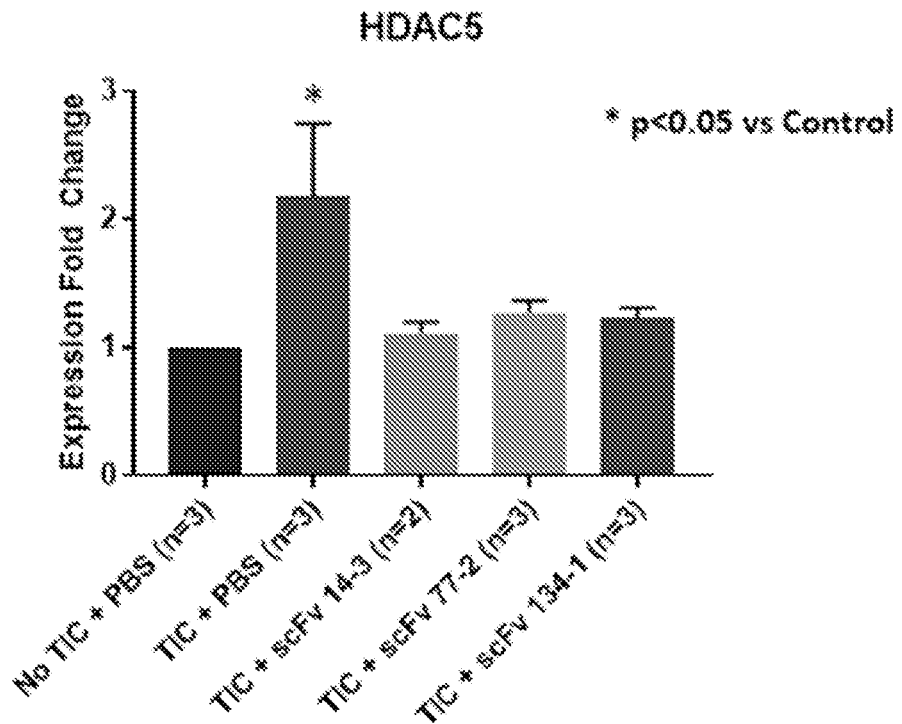

FIG. 11. Trigeminal ganglia neuron RT-PCR. The expression of HDAC5 RNA was significantly increased in the trigeminal ganglia neurons of mice with chronic neuropathic pain (TIC+PBS) (week 10). The anti-CCK-B receptor scFv antibodies reduced expression of HDAC5 RNA to levels equivalent to naïve mice.

Figure 12:
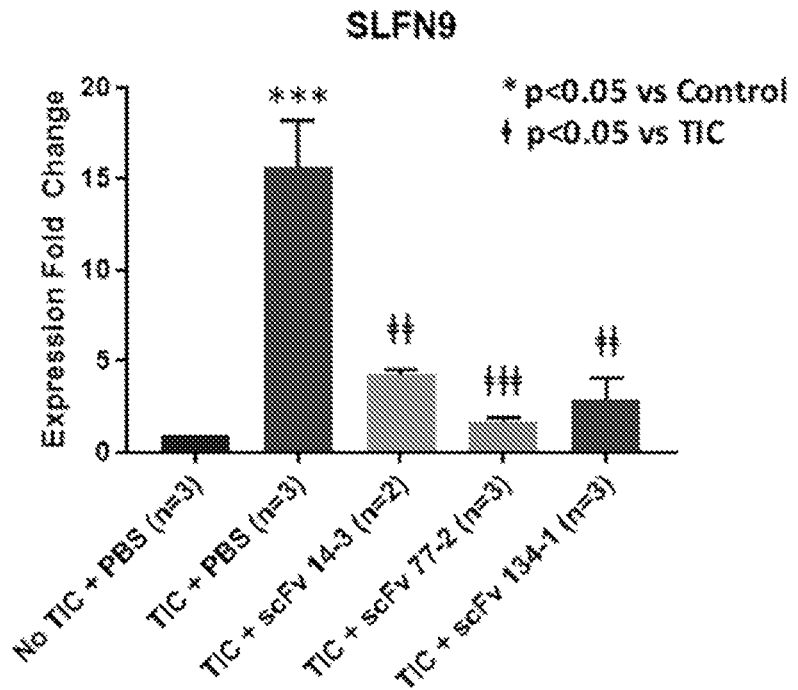

FIG. 12. Trigeminal ganglia neuron RT-PCR. The expression of Schlafen family member 9 (SLFN9) was significantly increased in the trigeminal ganglia neurons of mice with chronic neuropathic pain (TIC+PBS). The anti-CCK-B receptor scFvs reduced expression of SLFN9. SLFN9 expressed in mice has a human ortholog, Schlafen family member 13 (SLFN13). Schlafen family members increase T-cell activation and cellular proliferation promoted by inflammatory mediators tumor necrosis factor and interferon.

Figure 13:
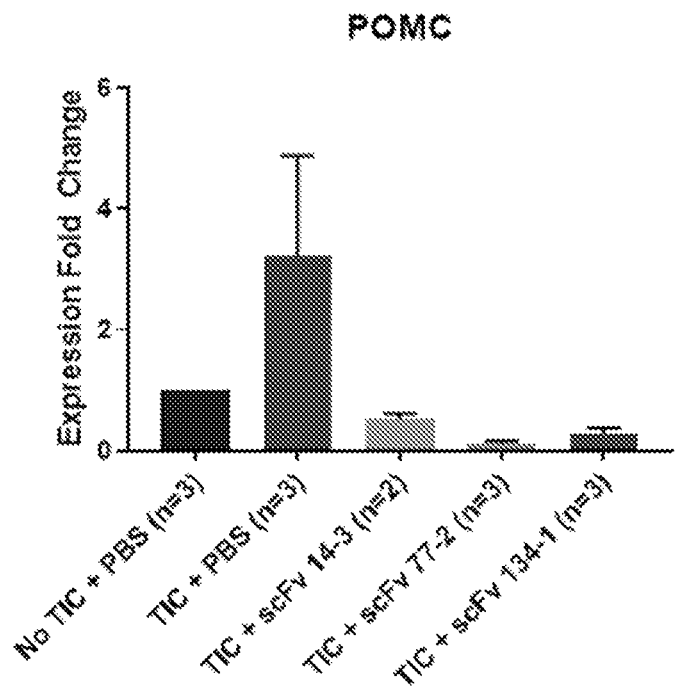

FIG. 13. Trigeminal ganglia neuron RT-PCR. Pro-opiomelanocortin (POMC) RNA trended toward an increase in the trigeminal ganglia neurons of mice with chronic neuropathic pain (TIC+PBS). Treatment with all of the anti-CCK-B receptor scFvs reduced expression to levels similar to naïve mice given the PBS vehicle. POMC is the polypeptide hormone precursor to cortisol, and endogenous opioids met-encephalin, leu-encephalin, and beta-endorphin.

DETAILED DESCRIPTION OF ILLUSTRATIVE EMBODIMENTS

This disclosure describes the generation and use of effective non-addictive, non-opioid therapeutics. Such therapeutics can be tailored to specific pain syndromes. While described herein in the context of an exemplary embodiment in which the target of the therapeutic is the cholecystokinin B (CCK-B) receptor, the generation platform and methods can be used to create alternative therapeutics using other targets. Exemplary other targets include, for example, other pain-related receptors that increase with pain, cytokine/chemokine receptor (e.g., CX3CR1 fractalkine receptor); or any receptor that results downstream in generating pain (e.g., TLR4, glycine receptor, glutamate receptors (NMDA receptor, AMPA receptor, kianate receptors), or $GABA_A$ receptor.

Activating CCK-B receptors produces pain in humans. Overactivation of the nociceptive system by noxious stimuli such as inflammatory or peripheral nerve injury increases CCK-B receptors in neuronal ganglia and can be blocked by scFv antibodies. The scFv therapeutics described herein can enhance physiological analgesia for treating conditions with both inflammatory and neuropathic pain. Gene profiling revealed significant increases in cholecystokinin B (CCK-B) receptor gene expression after treatment with anti-CCK-B receptor scFv antibodies in the trigeminal ganglia in the trigeminal nerve injury mouse model (FIG. 10). The two-fold increases in HDAC5 and POMC RNA (FIG. 11, FIG. 13) and the approximately seven-fold increase in SLFN9 RNA (FIG. 12) were absent after treatment with all of the anti-CCK-B receptor scFv antibodies.

Figure 2E:
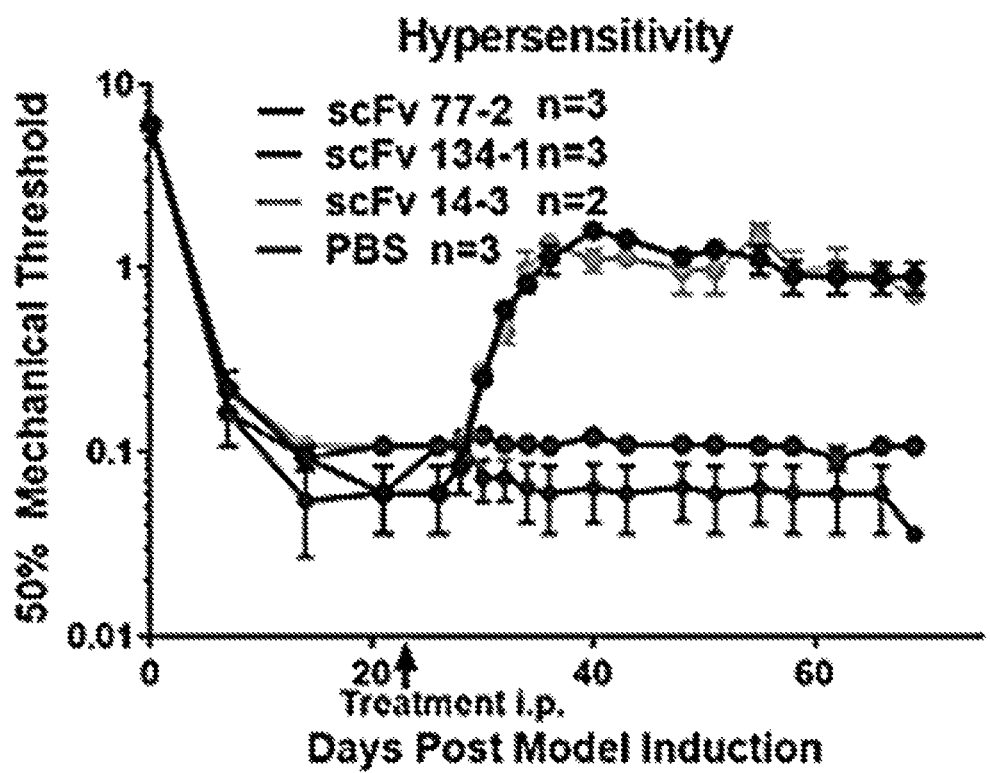
Figure 3:
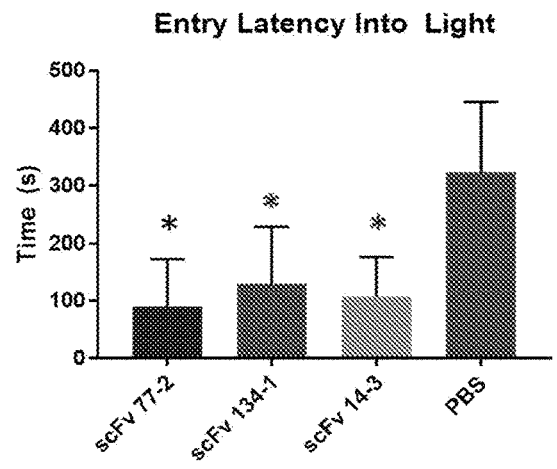
FIG. 3. Behavioral effects of anti-CCK-B receptor antibodies in a mouse model. (A) Mice with Trigeminal Inflammatory Compression (TIC) nerve injury treated with any one of the anti-CCK-B receptor scFv antibodies tested in week 8 post model induction had reduced anxiety measures compared to mice treated with the neutral phosphate buffered saline vehicle (PBS). (B) Mice with TIC nerve injury treated with anti-CCK-B receptor scFv 77-2 spent increased time grooming and licking the sucrose splashed on their rump and had a shorter latency to begin licking and grooming than mice treated with other scFvs or PBS, indicating less depression. In both (A) and (B), mice with TIC nerve injury were treated with anti-CCK-B receptor antibody at 4 mg/kg. scFv 77-2, n=2; scFv 134-1, n=3; scFv 14-2, n=2; PBS, n=3.
Figure 3:
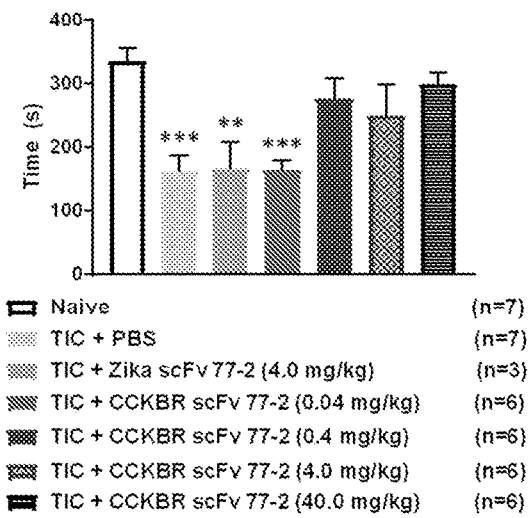
Figure 3:
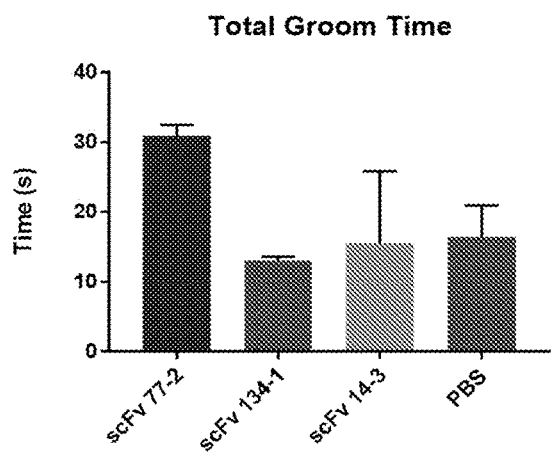
Figure 3:
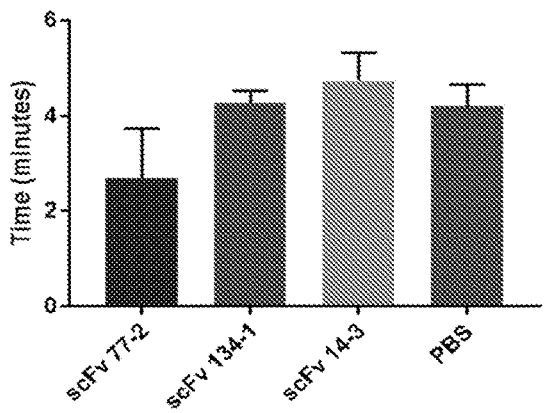
Figure 6:
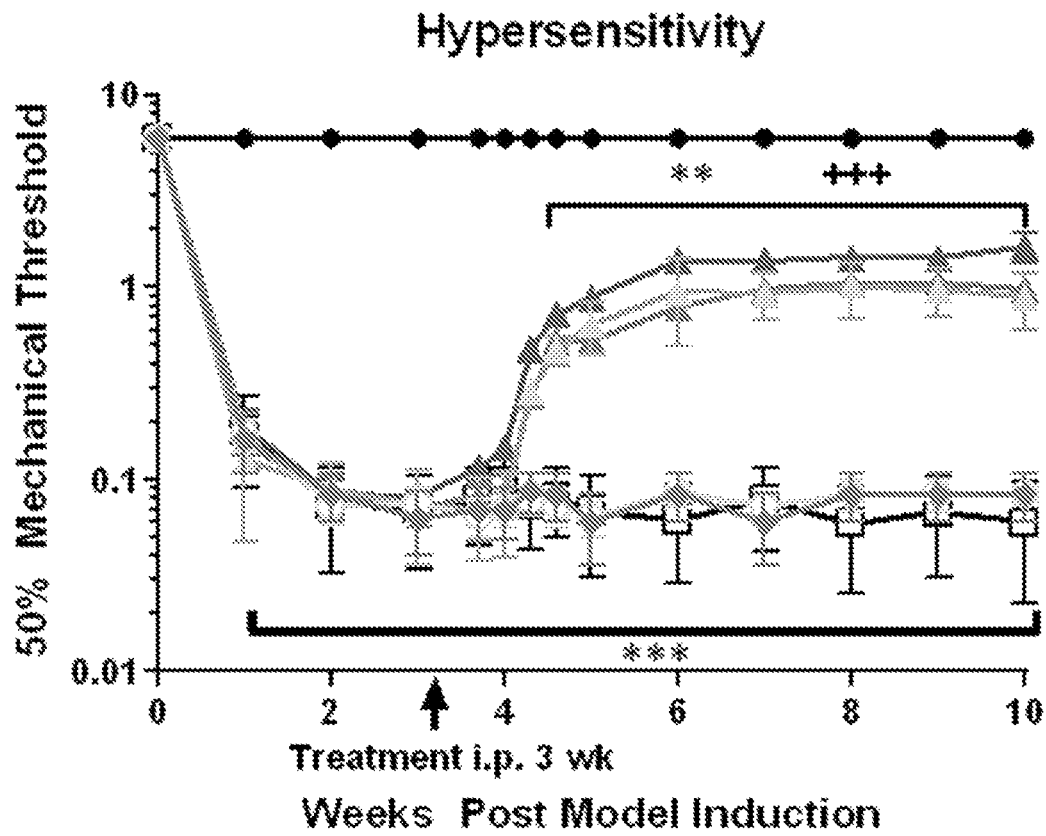
FIG. 6. Efficacy and binding specificity. (A) The dose response efficacy is shown for the three highest doses of the scFv 77-2 for reversal of mechanical hypersensitivity tested on the ipsilateral whisker pad (●, Naïve; light ▲, TIC+CCKBR scFv 77-2 0.4 mg/kg; medium ▲, TIC+CCKBR scFv 77-2 4.0 mg/kg; dark ▲, TIC+CCKBR scFv 77-2 40.0 mg/kg; ♦, TIC+Zika scFv 77-2 4.0 mg/kg; ○, TIC+CCKBR scFv 77-2 0.04 mg/kg; □, TIC+PBS. Zika scFv and the low dose (0.04 mg/kg) CCKBR scFv were ineffective. n=3; p<0.05 ANOVA. The pain was relieved in weeks 4-10 tested after nerve injury. P-values vs. naïve: p<0.01; *p<0.001. P-value vs TIC+PBS: +++p<0.001. (B) Binding specificity and cross-reactivity of anti-CCK-BR scFvs is shown by indirect ELISA. The three scFvs (scFv14-3, scFv 77-2, and scFv 134-1) demonstrated differential CCK-B receptor binding capability and specificity but did not cross-react with P2X4 receptor protein.
Figure 6:
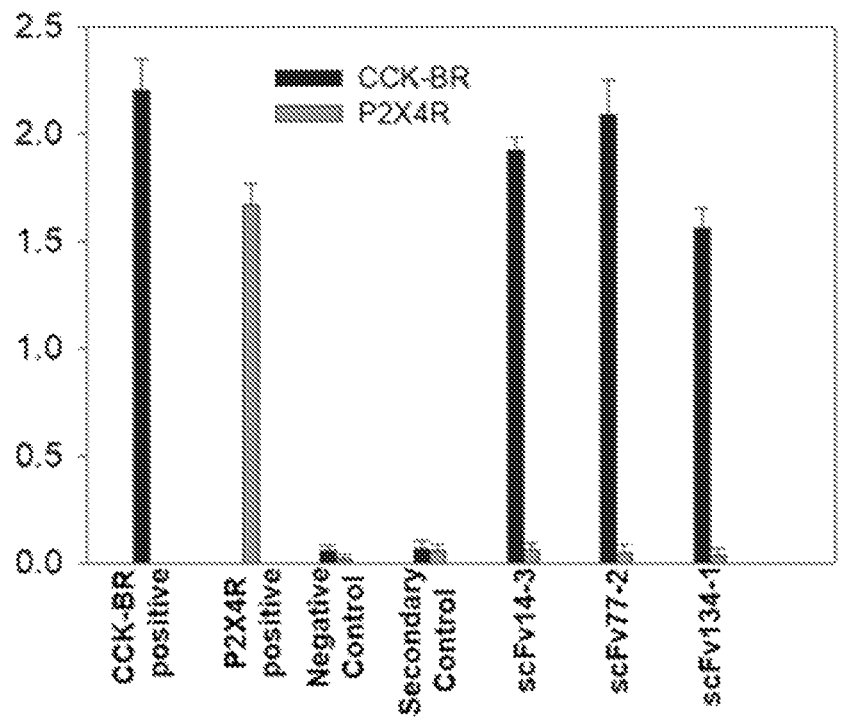

An exemplary brain-penetrant single-chain fragment variable (scFv) antibody, however, blocked CCK-B receptor activation and decreased mRNA content. As a result, scFv antibodies directed against the CCK-B receptor can reduce physiological pain, anxiety, and/or depression. This disclosure describes exemplary scFvs that block these behaviors in the mouse trigeminal inflammatory compression (TIC) nerve injury model (FIG. 2E, FIG. 3, FIG. 6A). The anti-nociceptive and anti-anxiety properties resembling the euphoric properties of exogenous opioid agonists of the μ-opioid receptor (MOR) and/or δ-opioid receptor (DOR) suggest that the exemplary CCK-B scFv antibodies described herein not only modulate pain but also modulate mood and anxiety. Thus, the CCK-B receptor is an ideal target for therapeutics that can affect nociceptive and/or aversive components of chronic pain in multiple pain syndromes.

Thus, the screening platform described herein allows one to generate a cabinet of, for example, non-opiate pain therapeutics, which can meet specific patient needs with awareness of mechanisms underlying the specific pain syndrome and sex differences. Improved pain management also can include adjuvants developed to improve effectiveness of low dose opioids. Chronic orofacial pain in particular has a poor therapeutic response rate (effective in 11-40% of patients) to analgesics (e.g., opioids, NSAIDS, gabapentin, carbamazepine, tricyclic antidepressants) in contrast to pain in other body regions, and thus remains a significant challenge. Traumatic blunt force injury to the face caused by motor vehicle accidents, military combat, dental surgery, and other events can sensitize the trigeminal nerve that innervates the head, dura, deep tissue, and tooth sockets. One consequence of nerve injury pain or "neuropathic pain" is transition to chronic pain. This may be largely due to the circuitry and mechanisms unique to the trigeminal nerve. Trigeminal innervation of the lateral parabrachial nucleus reportedly has direct connectivity with the limbic system via one synapse while spinal input crosses two synaptic connections. As another example, gene expression profiling results for trigeminal ganglia (TG) after nerve injury are notably different from that reported for sciatic nerve injury.

Chronic orofacial pain can be unrelenting and excruciating, reducing quality of life as well as diminishing physical and mental function. Chronic pain involves neuroplasticity, remodeling of brain reward/aversion circuitry, and gene expression alterations. Shifts in brain representation from nociceptive to limbic circuitry occur within 3-12 months. Altered connectivity with amygdala, medial prefrontal cortex (mPFC), and hippocampus evident with MRI is correlated with pain level in human pain patients.

This disclosure describes using a receptor whose activation elicits pain as a target for generating therapeutics effective for alleviating pain. In the embodiment exemplified herein, the cholecystokinin receptor (CCK-BR) is used as a target to generate non-opioid therapeutics effective for alleviating orofacial pain. Once again, however, while described in detail in the context of the exemplary embodiment in which the scFv therapeutics target CCK-B receptor, other non-opioid antagonist therapies can be generated that have other pain-eliciting targets—e.g., a receptor whose activation also elicits pain.

The CCK-B receptor is also implicated in anxiety-related behaviors that can accompany chronic pain. The CCK-B receptor and its neuropeptide ligand, CCK, are widely expressed in brain circuitry involved in stress, anxiety, reward/addiction, and cognition. Several patient studies and social stress rodent models use CCK to chemically induce experimental anxiety and panic attacks specifically to test novel pharmacological interventions. Conversely, blocking centrally active CCK-B receptors inhibits development of anxiety-like and fear-like behaviors as well as inhibits CCK release in the medial prefrontal cortex (mPFC). Sites with high levels of CCK-B receptor expression overlap with pain circuitry in the trigeminal ganglia, mPFC, and rostroventral medulla (RVM), a brainstem serotoninergic pain modulation site.

CCK-B receptors also are involved in homeostasis of the supraspinal opioid system. For example, injecting CCK-B receptor blockers/antagonists into the RVM reverses anxiety indicia that are induced by opioid withdrawal in rats. Treatments that specifically block CCK-B receptors suppress maintenance and reactivation of morphine dependence in place preference tests. Pharmacological ablation of CCK-B receptor expressing cells in mouse RVM inhibits descending pain facilitation and reverses somatic chronic constriction injury (CCI) induced hypersensitivity. CCK-B receptor mRNA expression is upregulated in a mouse hindpaw burn injury model and while morphine had little efficacy, proglumide—a clinically used non-specific blocker for both CCK-A and CCK-B receptors—reduced hypersensitivity. Naïve CCK-B receptor deficient mice (CCK-BR KO) are mechanically hyposensitive after sciatic nerve CCI. Thus, treatment with anti-CCK-B receptor scFvs would likewise be effective for treatment of alcohol withdrawal, acute pain, and chronic pain in other body regions.

A role for CCK-B receptors, specifically, in orofacial pain has remained relatively unexplored until recently. Using microarray gene expression profiling amenable to targeted therapy approach, expression of the CCK-B receptor gene (Cckbr) increases more than 2.7-fold in trigeminal ganglia three weeks after mouse trigeminal nerve injury (p<0.0009; false discovery rate of 5% (q>0.0075). Gene expression profiling found that elements of the immune response are not activated in CCK-B receptor KO mice in a somatic CCI model. Upregulation of TLR4 and IL-1β expression in wild-type mice is absent in CCK-B receptor KO mice, suggesting that the CCK-B receptor has a role in regulating innate immunity. Alternatively, this may indicate that effectively blocking pain transmission significantly reduces the innate immune response.

While described herein in the context of an exemplary embodiment in which the therapeutic is a single-chain variable fragment (scFv), the compositions described herein can provide other forms of antibodies. Generally, the therapeutic can include any suitable antibody generated against the intended target. As used herein, "antibody" refers to a molecule that contains at least one antigen binding site that immunospecifically binds to a particular antigen target of interest. The term "antibody" thus includes but is not limited to a full length antibody and/or its variants, a fragment thereof, peptibodies and variants thereof, monoclonal antibodies (including full-length monoclonal antibodies), polyclonal antibodies, multispecific antibodies (e.g., bispecific antibodies) formed from at least two intact antibodies, human antibodies, humanized antibodies, and antibody mimetics that mimic the structure and/or function of an antibody or a specified fragment or portion thereof, including single chain antibodies and fragments thereof. Thus, as used herein, the term "antibody" encompasses antibody fragments capable of binding to a biological molecule (such as an antigen or receptor) or a portion thereof, including but not limited to Fab, Fab' and F(ab')$_2$, pFc', Fd, a single domain antibody (sdAb), a variable fragment (Fv), a single-chain variable fragment (scFv) or a disulfide-linked Fv (sdFv); a diabody or a bivalent diabody; a linear antibody; a single-chain antibody molecule; and a multispecific antibody formed from antibody fragments. The antibody can be of any type (e.g., IgG, IgE, IgM, IgD, IgA and IgY), class (e.g., IgG1, IgG2, IgG3, IgG4, IgA1 and IgA2), or subclass.

Translationally-relevant scFv antibodies that block CCK-B receptors may be generated using a modified cell-free ribosome display technology (Markiv et al., 2011, *BMC Biotechnol.* 11:117; Kunamneni et al., 2018, *PLoS ONE* 13(11):e0205743; Kunamneni et al., 2019, *Am. J. Trop. Med. Hyg.* 101(1):198-206), and CCK-B receptor (Kunamneni et al., 2019, *FASEB Journal*, April 2019, Published Abstract Number Ib31; Kunamneni et al., 2019, "Therapeutic scFv antibody for the treatment of neuropathic pain and anxiety." Society for Neurosciences annual meeting. Chicago, IL, Oct. 17-23, 2019, #661.18). The ribosome display method can produce repertoires of high-affinity antibodies against a target peptide, in this case, an extracellular 15-amino-acid peptide fragment of the CCK-B receptor (SEQ ID NO:2). The modified cell-free ribosome display scFv antibody technology replaces time intensive hybridoma monoclonal antibody development. The ribosome display technology is capable of reliably synthesizing and rapidly expressing practically unlimited quantities of antibodies. This scFv antibody technology is well known for its potential to efficiently provide therapeutic antibodies with high specificity, persisting effects, and small size (~25 kD) for better tissue penetration compared to whole IgG (~150 kD). In some embodiments, the antibodies can be brain penetrant to allow for use as pain therapy.

In some embodiments, the scFv antibodies can be readily modified to incorporate intrinsic fluorescence and other modification to allow for, for example, easy detection histologically or in vivo using image scanners. Fluorescently tagged scFv antibodies ("fluobodies") can be modified to possess intrinsic fluorescence by cloning a functional portion of a fluorescent protein—e.g., monomeric red fluorescent protein (RFP1). The fluorescent tag provides optical (excitation/emission 584/607 nm) and physical (photo- and pH 5-11 stable) properties that facilitate in vivo Imaging System (IVIS) and post-mortem dual label neuropathology.

Figure 1:
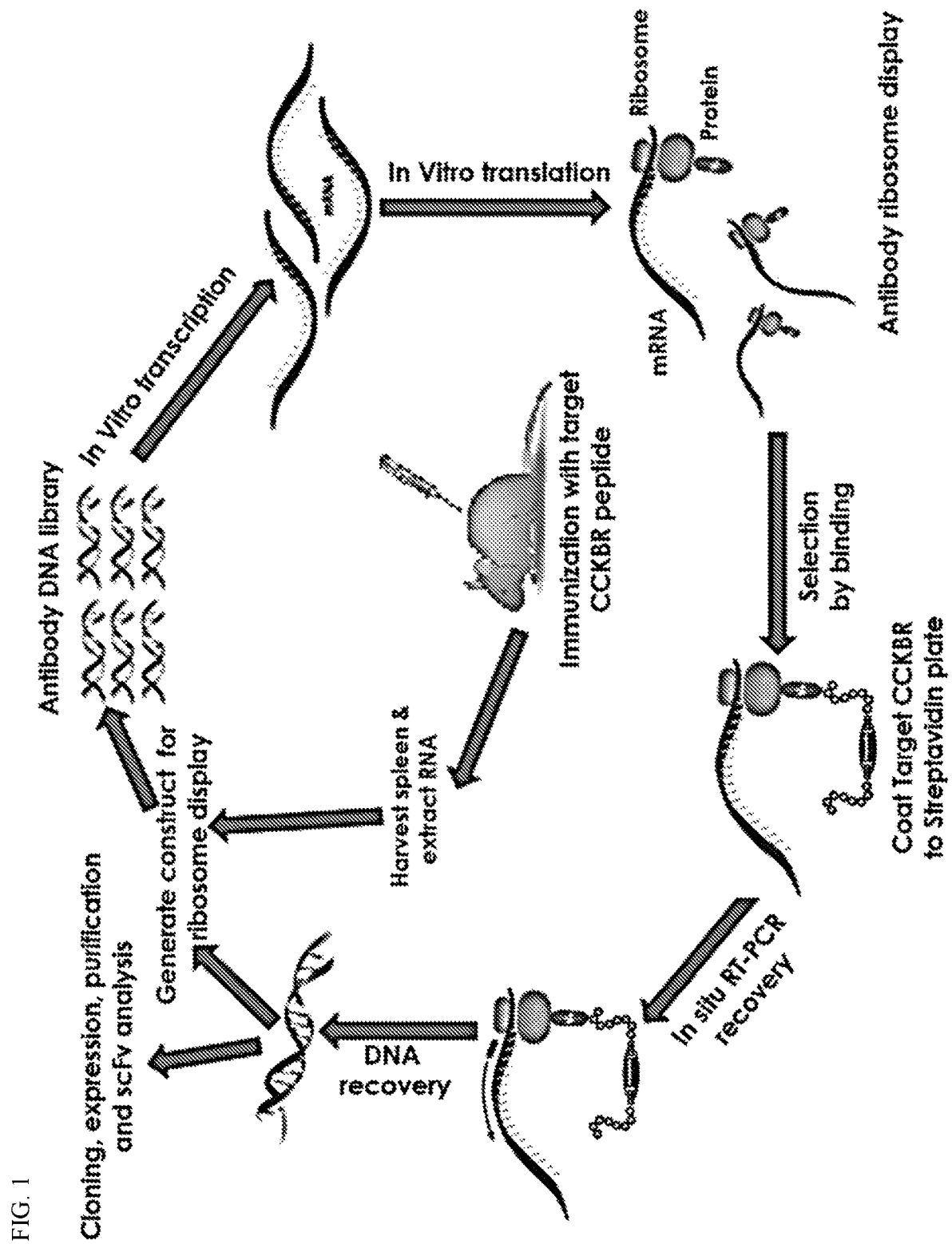
FIG. 1. Generation of scFv antibodies. scFv antibodies are generated using cell-free ribosome display from mice immunized with a model target, a 15-amino-acid extracellular CCK-B receptor peptide, CETPRIRGTGTRELE (SEQ ID NO:2).

FIG. 1 provides a schematic overview of the method for generating scFv antibodies that bind to a target peptide. A combinatorial library of VH and VL genes is generated by PCR from spleens of mice immunized with a target peptide. In the illustrated exemplary embodiment, the target peptide is an extracellular 15-amino-acid CCK-B receptor peptide fragment, SEQ ID NO:2. scFv antibodies that specifically bind to the target peptide are selected by, for example, immobilizing the target peptide to a substrate—e.g., biotinylating the peptide and immobilizing the biotinylated peptide to a streptavidin-coated plate. The coupled in vitro transcription/translation reactions are performed on the scFv antibody library. Since these templates have the terminal stop codon removed, the protein ribosome complex will stall, thus retaining the mRNA. The resulting preformed tripartite antibody ribosome mRNA (ARM) complexes are incubated in "target"-coated tubes. After a desired number of rounds of selection—e.g., three rounds of selection—the retained antibody ARM complexes are recovered by RT-PCR (~750 bp). The enriched antibody genes are subcloned into an expression vector (e.g., pGEM T-Easy; Promega Corp., Madison, WI) and transformed into X L1-Blue *Escherichia coli* (*E. coli*).

In this case, about 1000 white colonies were selected from the scFv library and 30% randomly chosen clones were sequenced to identify unique antibody clones and the VH and VL sequences determined. Putative genes encoding selected scFv antibodies that specifically bind to the target peptide are subcloned (e.g., into a pET32a plasmid) for cytoplasmic expression in an expression microbe (e.g., *E. coli*). About 100 colonies were selected and screened for the presence of specific scFv antibodies with an indirect ELISA using an optical density-based screening method of crude lysates (primary screening). Selection of scFv candidates is based on the ratio of the scFv absorbance value to that of the positive control under similar conditions using the CCK-B receptor peptide ELISA Kit (MyBioSource, Inc., San Diego, CA).

Finally, scFv candidates from the primary screening were expressed, purified, and the affinity of each scFv was determined (e.g., by surface plasmon resonance (SPR) microarrays (secondary screening)) to determine kinetic constants ($k_{on}$ and $k_{off}$). Affinity ranking is defined as the ratio of the scFv $K_D$ value to that of the positive control under the same conditions. scFv antibodies displaying desired binding kinetics were then tested for therapeutic efficacy. In the exemplary embodiment shown in FIG. 1, candidate scFv antibodies showing desired binding against the CCK-B receptor from the secondary screening were tested as pain therapy in the trigeminal nerve injury model.

scFv antibodies can be expressed to include a modification (e.g., a 6×HIS tag) to simplify isolation after expression from an expression vector (e.g., pET32a) in a host microbe (e.g., *E. coli*). The expression plasmid may be transfected into a host microbe (e.g., Rosetta gamiB(DE3) competent cells), expressed, and the scFv antibody purified using a purification strategy appropriate for use with any modification of the scFv to aid in isolating the scFv. In the case of a 6×HIS tag, a 1 mL HisTrap column (GE Healthcare, Chicago, IL) may be used to isolate the scFv antibodies.

Figure 2A:
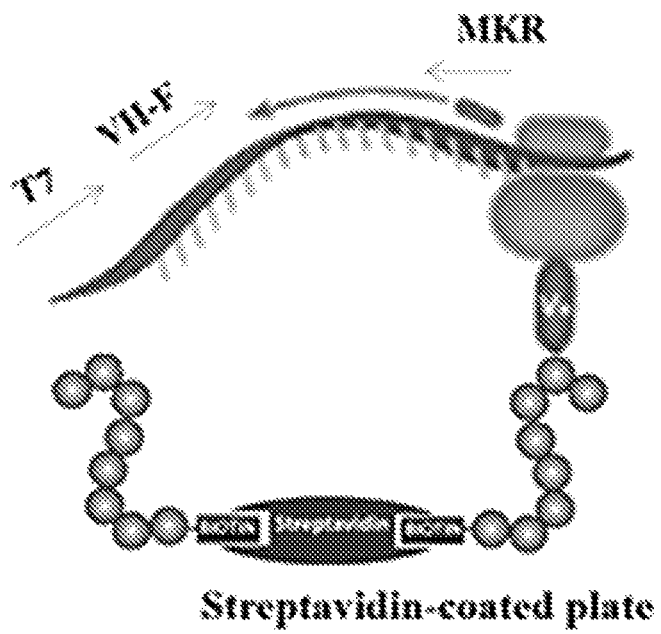
FIG. 2. Isolation and efficacy of anti-CCK-B receptor antibodies. (A) Schematic of stalled ARM complex and position of primers used for RT-PCR recovery in the first, second, and third cycles of ribosome display. (B) Analysis of RT-PCR recovery of VH/K cDNA from CCK-B receptor immunized spleen in the first, second, and third cycles. (C) Western blot of eight purified unique CCK-B receptor scFv antibodies generated by cell-free ribosome display. (D) CCK-B receptor binding affinity of the three purified scFvs with the highest binding affinities. ●, scFv14-3; ■, scFv77-2; ▲, ScFv134-1. (E) Two scFvs effectively reversed the induced orofacial neuropathic pain indefinitely, indicated by an increase in the mechanical threshold. The mechanical threshold was significantly increased after a single dose of scFv 77-2 or scFv 14-3 compared to PBS tested three weeks post trigeminal nerve injury. The scFv 134-1 antibody was ineffective (100 µg, n=3, p=0.0001).
Figure 2B:
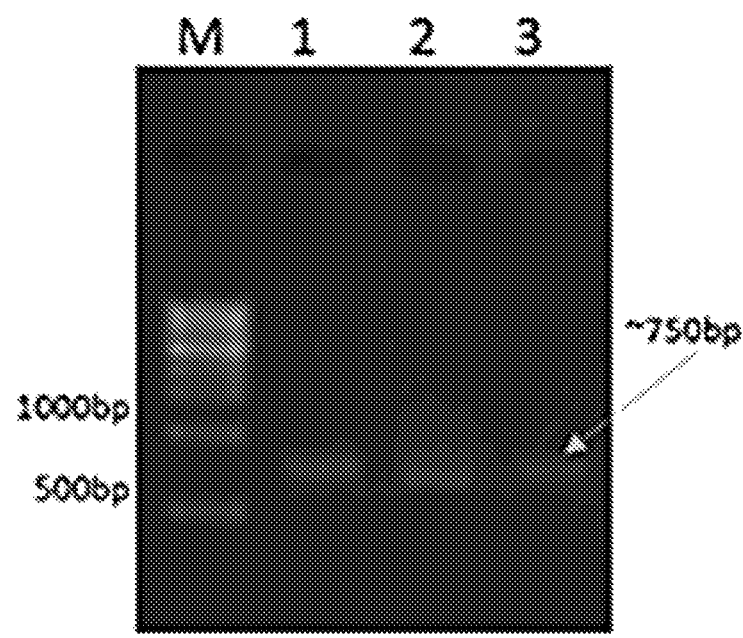
Figure 2C:
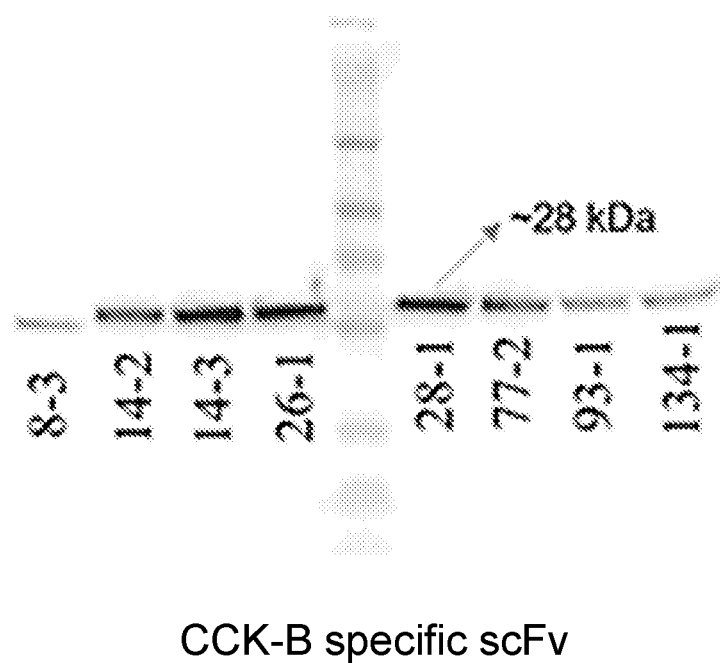
Figure 2D:
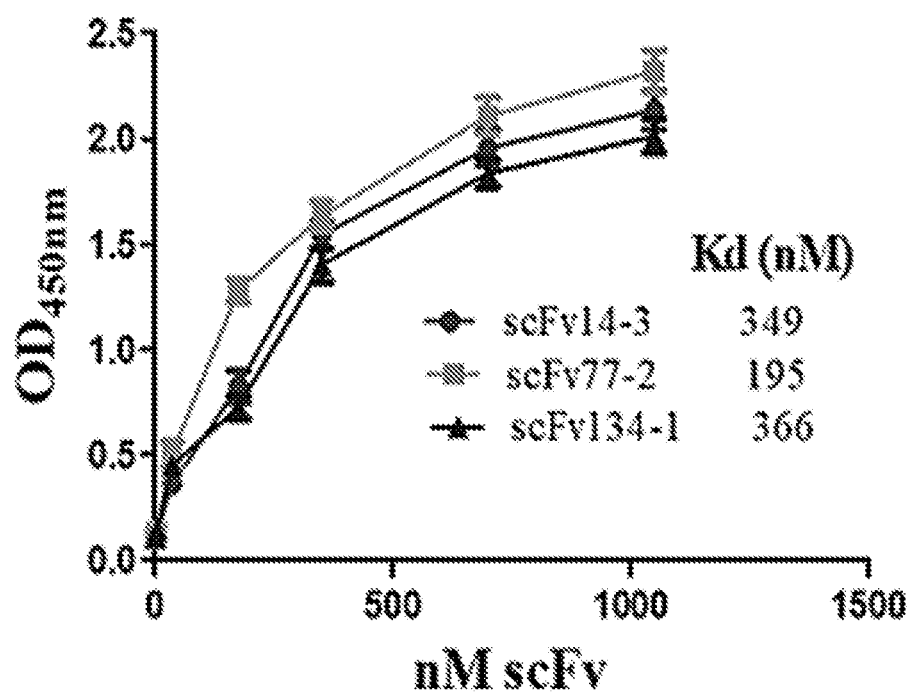

Binding of scFv antibodies to the target peptide can be determined by Western blot and/or ELISA analyses (FIG. 2C, 2D). The scFv clones showing high reactivity can be further analyzed for cross-reactivity against proteins related to the target peptide. In the case of scFv antibodies generated against a CCK-B receptor peptide, this may be done to select for CCK-B receptor-specific antibodies. FIG. 6B shows that three anti-CCK-B receptor scFvs specifically bind to CCK-B receptor, but do not bind to the P2X4 receptor.

The scFv antibodies can then be tested for therapeutic activity. In the case of scFv antibodies that bind CCK-B receptor, the scFv antibodies may be tested for analgesic activity. Those with analgesic activity can further be modified to include a fluorescent tag to assist with, for example, the histological analysis. A fluorescent tag (e.g., RFP1) allows histological examination of the scFv and potentially IVIS visualization of the bound antibody in, for example, an animal model—e.g., white mice.

For example, using the exemplary CCK-B receptor model illustrated in FIG. 1, eight scFv antibodies that neutralize the CCK-B receptor were identified (SEQ ID NOs:3-10). The eight scFv antibodies identified demonstrated differential CCK-B receptor-binding capability and specificity by indirect ELISA tests. This assay was specific for CCK-B receptor peptide, and a negative control anti-EBOV scFv4-2 antibody developed previously did not react. Of the eight newly generated scFv antibodies against the CCK-B receptor, scFv77-2, scFv14-3, and scFv134-1 had the highest affinity, whereas others had lower affinity (not shown), reflecting that the panning was efficient in selecting clones of high affinity (FIG. 2D). The three high affinity CCK-B receptor scFv antibodies were selected for in vivo testing. Successful development of scFv antibody that reduces mechanical hypersensitivity is presented as evidence of our potential to provide translational pain relief therapy (FIG. 2E), whereas an anti-Zika had no effect.

The scFv antibodies were tested for efficacy to reduce acute/chronic pain-related and anxiety-related behaviors and the neuropathology observed that is associated with chronic trigeminal nerve injury (FIG. 2E). Clinically, chronic orofacial pain is more prevalent in female than male patients. Relatively recent awareness that pain-related experimental read-outs can be different in males versus females necessitates testing in both male and female mice. Dose and immune responses may differ substantially by sex after nerve injury, while efficacy of the CCK-B receptor scFv antibody in behavioral assessments and effect on neuropathology will be similar. The nerve injury induces glial proliferation and loss of neurons in the medial prefrontal cortex (mPFC), as well as dysfunctional tau neuropathology in the hippocampus. CCK-B receptor scFv antibody treatment may reduce these nerve injury effects.

The orofacial neuropathic pain model used allows assessment of therapeutic effects at an acute time point and a chronic time point. In the model, week 8-9 mice have experienced pain equivalent to 12-14 human years and can be considered chronic. scFv antibodies can remain efficacious over an extended period of time (weeks) and are visible by IVIS for 8-14 days after a single treatment.

Three of the eight antibodies generated with strong signals in ELISAs were tested in a preliminary efficacy study for ability to reduce mechanical hypersensitivity (i.p., 100 μl). FIG. 2E shows a reduction of hypersensitivity for anti-CCK-B receptor antibodies scFv 14-3 and scFv 77-22. After giving a single dose of antibodies three weeks after trigeminal nerve injury, mechanical hypersensitivity reversed over subsequent weeks reminiscent of natural healing. While the scFv 134-1 was ineffective for blocking mechanical hypersensitivity, it was as effective as the other anti-CCK-B receptor scFv antibodies as an anti-anxiety therapy with decreased latency to enter the lighted side of the test box (FIG. 3A, left. The light side occupancy time was not significantly different from the naive control mice after treatment with the three highest doses of the 77-2 anti-CCK-B receptor scFv antibody indicating its efficacy for treatment of anxiety (FIG. 3A, right). FIG. 3B indicates a trend for the 77-2 anti-CCK-B receptor scFv antibody to improve depression after treatment.

Figure 4:
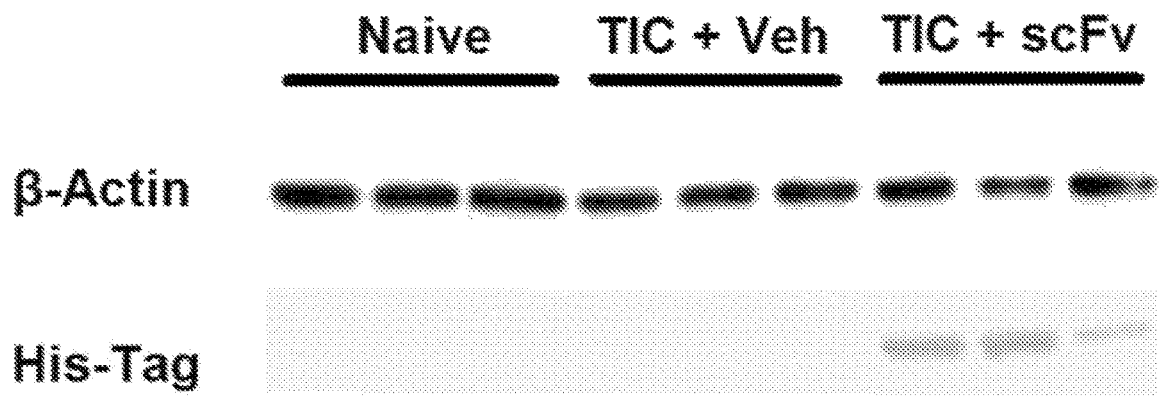
FIG. 4. Brain penetrance. The presence of the His-tag bound to the anti-CCK-B receptor scFv in the brain is evident by Western blot. The His-tag remaining in the brainstem (medulla) seven weeks after the single intraperitoneal dose indicates the anti-CCK-B receptor scFv is brain penetrant.

FIG. 4 demonstrates the presence of the His-tag bound to the anti-CCK-B receptor scFv in the brain. The His-tag remains in the brainstem (medulla) 7 weeks after the single intraperitoneal dose indicating brain penetration of the anti-CCK-B receptor scFv.

Figure 5:
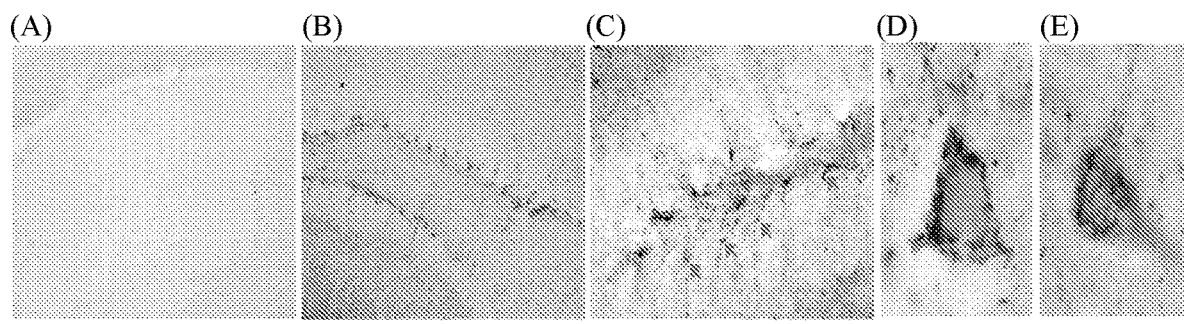
FIG. 5. Hyperphosphorylated (PHF-1) Tau protein expression in the limbic hippocampal cortex. (A) No hyperphosphorylated PHF-1 tau protein is observed in naive mice (200×). (B) Ten weeks post nerve injury, PHF-1 tau is detected in neurites penetrating through the molecular layers (200×). (C) The arrows indicate granular inclusions in the dentate gyrus neurites (400×). (D and E) Higher power views of PHF-1 in limbic hippocampal CA3 neurons (600×).

CCK-B receptor antibody treatment can reduce the pathological increases in hyperphosphorylated tau (pS396/S404 tau) and related tau kinase pERK, and pPERK that are observed in the chronic pain model using validated antibodies (FIG. 5). These proteins are increased in stroke, head injury, and dementias, thus the scFv therapeutics also may be relevant for treating one or more of these indications.

FIG. 6A, FIG. 7, FIG. 8, and FIG. 9 show dose-dependent effects of anti-CCK-B receptor scFv 77-2. FIG. 6A shows the dose response effect of scFv 77-2 on reducing neuropathic pain, as measured by ipsilateral reversal of mechanical hypersensitivity. FIG. 7 demonstrates the effect of increasing doses of anti-CCK-B receptor scFv 77-2 which bind to trigeminal neurons in culture thus blocking/reducing the ability to bind of a commercial antibody with a fluorescent tag. The ability of the anti-CCK-B receptor scFv to bind specifically on the CCK-B receptor site on the neurons in a dose dependent manner is confirmed by the reduced immunocytochemical staining. FIG. 8 shows the dose-dependent efficacy of anti-CCK-B receptor scFv 77-2 for anxiety reduction, as measured with the light/dark box in the trigeminal inflammatory compression (TIC) model. FIG. 9 shows the dose-dependent efficacy of svFv 77-2 for reducing depression behavior, as measured in the sucrose splash test for depression.

FIG. 10 shows that treatment with anti-CCK-B receptor scFv antibody reduces the CCK-B receptor mRNA (RT-PCR). Treatment of mice with scFv 77-2 or scFv 14-3 in the trigeminal inflammatory compression (TIC) model reduced CCK-B receptor mRNA transcripts, while CCK-B receptor RNA remained elevated with the scFv 134-1 that also failed to reduce mechanical allodynia.

FIG. 11 shows that treatment with an anti-CCKB receptor scFv reduces expression of histone deacetylase 5 (HDAC5) in the trigeminal inflammatory compression (TIC) model. HDAC5 is a member of class IIa histone deacetylase (HDAC) isozymes, having functions in transcriptional regulation, cell proliferation, cell cycle progression, and cellular developmental activities. HDAC5 also is involved in many diseases including cancer. Histones play a critical role in transcriptional regulation cell cycle progression and developmental events. Histone acetylation/deacetylation alters chromosome structure and affects transcription factor access to DNA. HDAC5 possesses histone deacetylase activity and represses transcription. The repression of HDAC5 would make the anti-CCK-B receptor scFv a potential therapeutic candidate for HDAC5-mediated diseases such as colon cancer. During chronic pain, HDAC5 would attempt to reduce cellular stress generation of reactive oxygen species to reduce DNA damage and potential for alterations resulting in cancer.

Similarly, FIG. 12 shows that treatment with an anti-CCK-B receptor scFv reduces expression of Schlafen family member 9 (SLFN9). SLFN9 is expressed in mice and has a human ortholog, Schlafen family member 13 (SLFN13). SLFN9 is an endoribonuclease that cleaves tRNAs and rRNAs. While the function of SLFN9 is currently unknown, knockdown of related Schlafen family members reduce T cell activation promoted by inflammatory mediators tumor necrosis factor and interferon. Thus, anti-CCK-B receptor scFv may reduce the immune response known to accompany and aggravate neuropathic pain.

FIG. 13 shows that treatment with an anti-CCKB receptor scFv reduces expression of pro-opiomelanocortin (POMC). POMC is a polypeptide hormone precursor to cortisol, met-encephalin, leu-encephalin, and beta-endorphin. Reduction of cortisol provides the positive effect of anti-CCKB receptor scFv in reduction of anxiety (FIG. 8).

Thus, this disclosure describes therapeutics that may be used to treat pain, including direct treatment of pain and/or anxiety-related and/or depression-related behaviors observed with chronic or persistent pain. In some embodiments, the therapeutic can be an scFv that targets the CCKB receptor such as, for example, an scFv that includes the amino acid sequence of any one of SEQ ID NO:3, SEQ ID NO:4, SEQ ID NO:5, SEQ ID NO:6, SEQ ID NO:7, SEQ ID NO:8, SEQ ID NO:9, or SEQ ID NO:10. Once again, however, while exemplified in the context of the exemplary embodiment in which the therapeutic is an scFv that targets the CCK-B receptor, other non-opioid antagonist therapies can be generated that have other pain-eliciting targets—e.g., a receptor whose activation also elicits pain. Exemplary other targets include, for example, other pain-related receptors that increase with pain, cytokine/chemokine receptor (e.g., CX3CR1 fractalkine receptor); or any receptor that results downstream in generating pain (e.g., TLR4, glycine receptor, glutamate receptors (NMDA receptor, AMPA receptor, kianate receptors), or $GABA_A$ receptor.

The scFv antibodies described herein may be formulated with a pharmaceutically acceptable carrier to form a therapeutic pharmaceutical composition. As used herein, "carrier" includes any solvent, dispersion medium, vehicle, coating, diluent, antibacterial, and/or antifungal agent, isotonic agent, absorption delaying agent, buffer, carrier solution, suspension, colloid, and the like. The use of such media and/or agents for pharmaceutical active substances is well known in the art. Except insofar as any conventional media or agent is incompatible with the active ingredient, its use in the therapeutic compositions is contemplated. Supplementary active ingredients also can be incorporated into the compositions. As used herein, "pharmaceutically acceptable" refers to a material that is not biologically or otherwise undesirable, i.e., the material may be administered to an individual along with the scFv antibody without causing any undesirable biological effects or interacting in a deleterious manner with any of the other components of the pharmaceutical composition in which it is contained.

A pharmaceutical composition may be formulated in a variety of forms adapted to a preferred route of administration. Thus, a composition can be administered via known routes including, for example, oral, parenteral (e.g., intradermal, transcutaneous, subcutaneous, intramuscular, intravenous, intraperitoneal, etc.), or topical (e.g., intranasal, intrapulmonary, intramammary, intravaginal, intrauterine, intradermal, transcutaneous, rectally, etc.). A pharmaceutical composition can be administered to a mucosal surface, such as by administration to, for example, the nasal or respiratory mucosa (e.g., by spray or aerosol). A composition also can be administered via a sustained or delayed release.

Thus, an scFv antibody may be provided in any suitable form including but not limited to a solution, a suspension, an emulsion, a spray, an aerosol, or any form of mixture. The composition may be delivered in formulation with any pharmaceutically acceptable excipient, carrier, or vehicle. For example, the formulation may be delivered in a conventional topical dosage form such as, for example, a cream, an ointment, an aerosol formulation, a non-aerosol spray, a gel, a lotion, and the like. The formulation may further include one or more additives including such as, for example, an adjuvant, a skin penetration enhancer, a colorant, a fragrance, a flavoring, a moisturizer, a thickener, and the like.

A formulation may be conveniently presented in unit dosage form and may be prepared by methods well known in the art of pharmacy. Methods of preparing a composition with a pharmaceutically acceptable carrier include the step of bringing the scFv antibody into association with a carrier that constitutes one or more accessory ingredients. In general, a formulation may be prepared by uniformly and/or intimately bringing the active compound into association with a liquid carrier, a finely divided solid carrier, or both, and then, if necessary, shaping the product into the desired formulations.

The amount of an scFv antibody administered can vary depending on various factors including, but not limited to, the specific scFv antibody being administered, whether the scFv antibody is being administered to treat pain or anxiety, the weight, physical condition, and/or age of the subject, and/or the route of administration. Thus, the absolute weight of scFv antibody included in a given unit dosage form can vary widely, and depends upon factors such as the species, age, weight and physical condition of the subject, and/or the method of administration. Accordingly, it is not practical to set forth generally the amount that constitutes an amount of scFv antibody effective for all possible applications. Those of ordinary skill in the art, however, can readily determine the appropriate amount with due consideration of such factors.

Generally, in some embodiments, the scFv antibody is administered in an amount effective to alleviate pain in the subject. As used herein, "alleviate" refers to any reduction in the extent, severity, frequency, and/or likelihood of pain experienced by the subject. In other embodiments, the scFv antibody is administered in an amount effective to reduce anxiety-related behaviors and/or depression-related behaviors observed after 6-8 weeks of persisting pain. As used herein, "anxiety-related behaviors and/or depression-related behaviors" in animals refer to measurement of excessive grooming events, avoidance of light, reduced exploration, and reduced exposure to novel or stressful conditions compared to control mice. These behaviors in rodents are measurable in the light/dark place preference test, open field exploratory test, and observable behaviors that can be quantified. Depression is measured in the sucrose splash test where mice with chronic pain are no longer interested in licking/grooming when 10% sucrose is sprayed on their rump. These behaviors in rodents are equivalent to human behaviors that include but are not limited to increased fidgeting, stereotypic movements, fears, avoidance, and dread measurable in the Beck Anxiety/Depression tests and the Daily Life Inventory.

In some embodiments, the method can include administering sufficient scFv antibody to provide a dose of, for example, about 100 ng/kg to about 500 mg/kg to a subject, although in some embodiments the methods may be performed by administering scFv antibody in a dose outside this range. Thus, in some embodiments, the method can include administering an scFv antibody in an amount effective to provide a minimum dose of at least 100 ng/kg, such as, for example, at least 500 ng/kg, at least 1 µg/gk, at least 5 µg/kg, at least 10 µg/kg, at least 25 µg/kg, at least 50 µg/kg, at least 75 µg/kg, at least 100 µg/kg, at least 250 µg/kg, at least 500 µg/kg, at least 1 mg/kg, at least 5 mg/kg, or at least 50 mg/kg. In some embodiments, the method can include administering an scFv antibody in an amount effective to provide a maximum dose of no more than 500 mg/kg, such as, for example, no more than 100 mg/kg, no more than 50 mg/kg, no more than 25 mg/kg, no more than 15 mg/kg, no more than 10 mg/kg, no more than 5 mg/kg, no more than 1 mg/kg, no more than 800 µg/kg, no more than 500 µg/kg, no more than 250 µg/kg, no more than 100 µg/kg, no more than 50 µg/kg, no more than 25 µg/kg, no more than 15 µg/kg, no more than 10 µg/kg, or no more than 5 µg/kg. In some embodiments, the method can include administering an scFv antibody in an amount effective to provide a dose that falls within a range having endpoints defined by any minimum dose listed above and any maximum dose listed above that is greater than the minimum dose. In some of these embodiments, the method includes administering sufficient scFv antibody to provide a dose of from about 10 µg/kg to about 5 mg/kg to the subject, for example, a dose of from about 100 µg/kg to about 1 mg/kg.

In some embodiments, an scFv antibody may be administered, for example, from a single dose to multiple doses per week, although in some embodiments the method can be performed by administering the scFv antibody at a frequency outside this range. When multiple doses are used within a certain period, the amount of each dose may be the same or different. For example, a dose of 1 mg per day may be administered as a single dose of 1 mg, two 0.5 mg doses, or as a first dose of 0.75 mg followed by a second dose of 0.25 mg. Also, when multiple doses are used within a certain period, the interval between doses may be the same or be different. In some embodiments, an scFv antibody may be administered in several doses of 100 µg/kg to 1 mg/kg.

In certain embodiments, an scFv antibody may be administered from about once per month to about five times per week. For example, an scFv antibody may be administered as a "once off" therapy. In other embodiments, an scFv antibody may be administered provide a dose of 1 mg/kg once per month; 100 µg/kg/daily; or 5 mg/kg/year.

In the exemplary embodiment in which the target of the scFv is the CCK-B receptor, the scFv may have clinical benefit beyond reducing pain. For example, CCK-B receptors expressed in the stomach are activated by gastrin to signal satiety. Inhibition in the GI system after 1-3 doses of the scFv antibody may augment appetite, at least on a short-term basis. Appetite increase and decreased anxiety would be welcome relief among cachexic patients with intractable chronic pain including terminal cancer pain, extending use for palliative care. As another example, cholecystokinin (CCK) and gastrin stimulate the growth of pancreatic cancer through the CCK-B receptor. Gastric cancer epithelial cells express CCK-B receptors that produce their own gastrin de novo, which in turn stimulates growth and metastases of gastric cancer by an autocrine mechanism. CCK-B receptors are overexpressed in gastric cancer. Thus, restoring CCK-B receptors to normal levels can reduce growth and metastases of gastric cancers and other gastrointestinal malignancies as well. The known association of *Helicobacter pylori* with predisposition to induce gastric cancer as well as stomach pain may indicate the scFv antibodies would be a preventative of pain and gastric cancer during treatment for the bacterial infection.

In the preceding description and following claims, the term "and/or" means one or all of the listed elements or a combination of any two or more of the listed elements; the terms "comprises," "comprising," and variations thereof are to be construed as open ended—i.e., additional elements or steps are optional and may or may not be present; unless otherwise specified, "a," "an," "the," and "at least one" are used interchangeably and mean one or more than one; and the recitations of numerical ranges by endpoints include all numbers subsumed within that range (e.g., 1 to 5 includes 1, 1.5, 2, 2.75, 3, 3.80, 4, 5, etc.).

In the preceding description, particular embodiments may be described in isolation for clarity. Unless otherwise expressly specified that the features of a particular embodiment are incompatible with the features of another embodiment, certain embodiments can include a combination of compatible features described herein in connection with one or more embodiments.

For any method disclosed herein that includes discrete steps, the steps may be conducted in any feasible order. And, as appropriate, any combination of two or more steps may be conducted simultaneously.

The present invention is illustrated by the following examples. It is to be understood that the particular examples, materials, amounts, and procedures are to be interpreted broadly in accordance with the scope and spirit of the invention as set forth herein.

EXAMPLES

Example 1

For ribosome display scFv antibody libraries, the cDNAs encoding immunoglobulin VH and VL regions joined by a 20-amino-acid flexible linker [$(G_4S)_4$] were constructed as previously described (Kunamneni et al. 2019, *FASEB J* 33: 1_supplement, 1b31-1b31) using total RNA isolated from the spleens from five mice immunized with a custom 15-amino-acid extracellular peptide fragment CETPRIRGTGTRELE (SEQ ID NO:2) with a biotin-tagged N-terminal, in N-methyl-2-pyrrolidone solvent) of the CCK-B receptor (GenScript, Piscataway, NJ) (4× i.p.).

The ribosome display scFv library was panned against CCK-B peptide with three rounds of selection. PCR products were cloned into pGEM T-Easy vector (Promega Corp., Madison, WI) and the VH-VL transformants (50 clones) were randomly selected for sequencing. This resulted in the isolation of a panel of eight CCK-B receptor recombinant antibodies that were subcloned into a pET32a vector, expressed, and purified from *E. coli* cytoplasm (FIG. 2C) as previously described (Kunamneni et al. 2019, *FASEB J* 33: 1_supplement, 1b31-1b31; Kunamneni et al., 2019, "Therapeutic scFv antibody for the treatment of neuropathic pain and anxiety." Society for Neurosciences annual meeting. Chicago, IL, Oct. 17-23, 2019, #661.18).

Example 2

Analytical Statistics

To achieve statistical significance, studies with n=6/group are repeated twice for authentication in both fixed and fresh tissue samples. Study groups for comparisons include naïve, surgical sham, and nerve injured male and female mice, w/wo scFv. T-tests or Friedman repeated ANOVA on ranks are used to analyze behavioral or expression changes. Groups are compared using a linear mixed model (LMM) for repeated measures design for between-(treatment groups) and within groups (time) effects. A compound symmetry assumption is used to model correlation among repeated measures taken on the same animal over time, but the LMM framework is flexible in this regard. In all cases $\alpha=0.05$ is accepted for significant differences.

CCK-B Receptor Localization

Immunohistological localization on the trigeminal cell membrane is anticipated using conventional methods with a commercially available CCK-B primary antibody (Cat #MBS421039, BioSource, Inc., San Diego, CA) and fluorescent tagged secondary antibody.

IVIS imaging examine the scFv antibody biodistribution in trigeminal ganglia (TG), brain, and other body regions. Mice are euthanized and perfused transcardially with buffered paraformaldehyde (4%). Quantitative immunohistology using computer assisted analysis (UNM Fluorescence Microscopy Shared Resource) examines CCK-B receptor scFv localization in TG, brainstem, and limbic structures, and the relationship to neurons and glia. Analysis of immunostaining in pathway structures is done in a minimum of five sections/region/animal to obtain mean staining intensities±standard error of the mean (SEM) for group comparisons. Dual immunostaining of neurons (NeuN) and differentiating biomarkers specific for glial cells (GFAP, Iba1) will identify pattern shifts along with the biodistribution of CCK-B receptor scFv antibodies in TG and limbic brain regions.

Immune Cell Flow Cytometry

Inflammation and nerve injury are established components of neuropathic pain. Blood is collected transcardially from deeply anesthetized mice, and mononuclear cells isolated. Cells labelled with fluorescent antibodies are quantified as outcome measures with standard flow cytometry methods in the UNM Shared Flow Cytometry and High Throughput Screening Resource. Comparisons to controls are made with and without scFv antibody therapy.

Trigeminal Nerve Injury Chronic Pain Model

The trigeminal nerve injury chronic pain model combines surgical incision with chemical irritation and compression of the trigeminal nerve provided by chromic gut suture. The model is induced in BALB/c mice by inserting 3 mm of chromic gut suture (4.0) into the tight space between the infraorbital branch of the trigeminal nerve and the bony infraorbital fissure through a small surgical incision made orally between the cheek and maxillary bone. Edema and injury develop in nerve fascicles in close proximity to the suture, simulating wound debris or blunt force traumatic injury. Whiskerpad hypersensitivity reliably develops within one week and persists at least six months determined by reflexive responses in von Frey filament testing. Cognitive dependent tests reveal anxiety at 6-8 weeks post injury with light/dark box place preference testing. Depression is also measurable at 6-8 weeks with the Sucrose Splash test. Recovery of learning can be determined with the Novel Object Recognition test. The white BALB/c mice are selected since they remain cooperative for chronic behavioral testing and can be imaged with IVIS since they lack pigment.

Dose Response

Dose response pilot reflexive mechanical threshold studies determined the optimal dose of the scFv antibodies with best efficacy to reduce trigeminal nerve injury induced pain-related behaviors. The pilot study control and nerve injured mice are treated intraperitoneally with a single dose (i.p., 0.04, 0.4, 4, and 40 in 10 µl, 100 µl, 200 µl volume respectively) of scFv antibody or vehicle. Mechanical hypersensitivity thresholds are determined weekly for comparisons to baseline.

The optimal CCK-B receptor scFv antibody dose is determined in week three for acute pain, or determined in separate cohorts at eight weeks for chronic pain. Optimal acute dose is determined when the single dose produces a plateaued mechanical sensitivity threshold closest to baseline responses. Optimal chronic dose is determined when repeated low doses return mechanical sensitivity to baseline response. Reflexive and cognitive dependent pain- and anxiety-related behaviors assess ability to reduce both development and maintenance phases of chronic pain.

Weekly behavioral testing continues for four weeks after treatment prior to euthanasia to insure pain-related and anxiety-related behaviors do not reappear. Any alteration in cognition due to the pain model and its recovery after scFv treatment is determined with the novel object recognition test. Other experimental read-outs include postmortem quantitative neuropathology, immune profile, RNA profile, and Western blots. Vaginal smears determine estrus cycle in the female mice.

PCR and Western Blot Authentication of Protein and Gene Status After Antibody

The RT-PCR determination of the RNA profile and the Western blot determination of the CCK-B protein content also assess the effectiveness of the scFv antibodies.

The TG, forebrain, and spleen cells are excised and prepared for Western blot assays, immunocytochemical localization, and RNA isolated for PCR. Assessment of mRNA content modified by the optimal scFv antibody is assessed by RT-PCR to evaluate expression changes.

Example 3

Cell-Free Ribosome Display

A combinatorial library of VH and VL genes was generated by PCR from spleens of mice immunized five times at three week intervals with a custom 15-amino-acid extracellular CCK-B receptor peptide fragment CETPRIR-GTGTRELE (SEQ ID NO:2) with a biotin-tagged N-terminal. Selection of CCK-B receptor scFv antibodies occurs as follows: (1) The CCK-B receptor peptide "target" (biotinylated) is used to coat the streptavidin plate. (2) The coupled in vitro transcription/translation reactions are performed on the scFv antibody library. Since these templates have the terminal stop codon removed, the protein ribosome complex will stall, thus retaining the mRNA. (3) The resulting preformed tripartite antibody ribosome mRNA (ARM) complexes are incubated in "target"-coated tubes. (4) After 3 rounds of selection, the retained antibody ARM complexes are recovered by RT-PCR (~750 bp). The enriched antibody genes are subcloned into pGEM T-Easy vector and transformed into X L1-Blue *Escherichia coli*. About 1000 white colonies are selected from the scFv library and 30% randomly chosen clones are sequenced to identify unique antibody clones and the VH and VL sequences determined. (5) Putative genes encoding selected scFv antibodies to the CCK-B receptor epitopes are subcloned into a pET32a plasmid for cytoplasmic expression in *E. coli*. About 100 colonies are selected and screened for the presence of specific scFv antibodies with an indirect ELISA using an optical density-based screening method of crude lysates (primary screening). (6) Selection of scFv candidates is based on the ratio of the scFv absorbance value to that of the positive control under similar conditions using the CCK-B receptor peptide ELISA Kit (MyBioSource). (7) Finally, scFv candidates from the primary screening are expressed, purified, and the affinity is determined by surface plasmon resonance (SPR) microarrays (secondary screening) to determine kinetic constants (kon and koff). Affinity ranking is defined as the ratio of the scFv KD value to that of the positive control under the same conditions. Ideal scFv antibodies against the CCK-B receptor from the secondary screening are tested as pain therapy in the trigeminal nerve injury model. Protein expression, purification, and authentication of scFv antibodies. CCK-B receptor scFv is expressed in the form of C-terminal 6×His fusion from the prokaryotic expression vector pET32a. The constructed pET32a plasmids are transfected into Rosetta gamiB (DE3) competent cells, expressed, and purified using 1 mL HisTrap HP columns (GE Healthcare). Binding of scFv antibodies to target CCK-B receptor is determined by Western blot and ELISA analyses. The scFv clones showing high reactivity are further analyzed for cross-reactivity against CCK family proteins. This is done in order to select for CCK-B receptor-specific antibodies with significant cross-reactivity to CCK-B receptor detected with ELISA after purification. The scFv antibody with the best analgesic potential will be selected for addition of a fluorescent tag to improve the histological analysis adapting a previously-described method (Markiv et al., 2011, *BMC Biotechnol.* 11:117). An RFP1 tag will allow histological examination of the scFv and potentially IVIS visualization of the bound antibody in white mice.

Western Blot

Protein content is assessed with Western blots using standard methods. Briefly, the sample protein is denaturation, followed by gel electrophoresis to separate proteins by molecular weight. A synthetic or animal-derived antibody (known as the primary antibody, typically commercially available) that recognizes and binds to the specific target protein is applied to the electrophoresis membrane. After washing off the antibody, a secondary antibody is added which recognizes and binds to the primary antibody. The secondary antibody is visualized through immunofluorescence probe attached to the secondary antibody, allowing indirect detection, validation, and quantitation of the specific target protein.

Reverse Transcription Polymerase Chain Reaction (RT-PCR)

RT-PCR is a technique commonly used in molecular biology to detect RNA expression. RT-PCR is used to qualitatively detect gene expression through the creation of complementary DNA (cDNA) transcripts from RNA. Relative quantification of RT-PCR involves the co-amplification of an internal control simultaneously with the gene of interest. An internal control is used to normalize the samples. Once normalized, a direct comparison of relative transcript abundances across multiple samples of mRNA can be made. The internal control must be chosen so that it is not affected by the experimental treatment. The results of the analysis are expressed as the ratios of gene signal to internal control signal, which the values can then be used for the comparison between the samples in the estimation of relative target RNA expression. When the cDNA binds to the double-stranded DNA of the PCR products, it will emit light upon excitation. The intensity of the fluorescence increases as the PCR products accumulate.

Trigeminal Inflammatory Compression (TIC) Nerve Injury Surgery

Mice undergo the trigeminal nerve injury as previously described (Ma et al., 2012, *Mol Brain* 5:44; Lyons et al., 2015, *Neuroscience* 295:126-138), except using an intraoral surgical approach, which is simpler than the previously described method. By making the small surgical incision intraorally rather than over the eye, the insertion of the chromic gut suture is easier, quicker (<5 minutes/mouse), and leaves no external indication of a surgery for better blinding of the study. Briefly, mice are anesthetized with isoflurane (2-3%), a small scalpel puncture is made at the gum line, and a piece of chromic gut suture (3 mm length, 4-0) is placed parallel to the infraorbital nerve (ION) and pushed into the infraorbital foramen. Mice with sham surgery receive anesthesia, the surgical procedure, but no chromic gut suture is put in place.

Experimental Read-Outs in Mice

Behavioral Assessment

To assess the efficacy of treatments, animals are subjected to different behavioral reflexive or cognitive dependent pain- and anxiety-related tests in order to quantify the therapeutic effect. Well-established, validated test instruments standard in the field are used for behavioral assessments. All behavioral assays are routine in the PI's laboratory (Lyons et al., 2015, *Neuroscience* 295:126-138; Lyons et al., 2017, *Clin J Pain* 33(12):1071-1080). All studies were performed by observers blinded to experimental groups. Testing nociceptive mechanisms involving specific nervous system circuitry can only be done in whole animal experiments. All mice undergo behavioral testing (naïve, surgical control, treatment mice). The behavioral tests are used to determine the degree of the sensitization by measuring reflexive and cognitive dependent behavioral responses. Reflexive withdrawal to noxious mechanical and thermal stimuli determines sensitivity thresholds reflective of the animal's nociceptive state. Cognitive dependent tests assess higher brain responses, including anxiety and stress level induced by the model. These standardized methods allow comparison among pain researchers of the efficacy of test compounds and partially fulfill requirements of the FDA for future approvals of use in humans. The methods are outlined below in more detail.

Reflexive Behavioral von Frey Fiber Assessment

Prior to testing, all animals are acclimated in the testing room in their home cage and to the tester over several weeks. Von Frey Assessment of Mechanical Sensitivity is performed before nerve injury to determine baseline thresholds and weekly after nerve injury to determine mechanical response thresholds using graded nylon filaments (von Frey filaments). Animals are moved from the housing room and acclimated in the testing room for 30 minutes in their home cages prior to testing. Animals are acclimated to gentle restraint (held in gloved hand for 10 min maximally) to test sensitivity to mechanical stimulation, i.e. withdrawal from probing with von Frey nylon monofilament fibers (1 hr maximum acclimatization and testing time). Sensitivity of the face to mechanical stimuli is quantified by measuring the number of head withdrawal events from graded thin nylon von Frey filaments with defined bending forces (tensile strength). Stimulation with the lowest fiber is not detectable on the back of the human hand; the largest fiber provides the sensation of a blunt paper clip wire end. Animals are free to voluntarily move their head away from the stimulus. The von Frey filament is applied over the whisker pad. A single trial consists of 5 applications of several selected mid-range von Frey filaments applied once every 3 to 4 seconds. If no positive response is evoked, the next stronger filament is applied. The mean occurrence of withdrawal events in each of the trials is expressed as the number of responses out of 5, 0 indicates no withdrawal, and 5 indicates the maximum number of withdrawals. An arithmetic algorithm is used to convert the fiber strength into grams force when three of five responses are evoked from a given fiber. Responses to decreased gram force compared to controls indicate decreased sensitivity threshold or "hypersensitivity".

In week 3 or 8, behavioral testing is followed by intraperitoneal antibody injections (or vehicle). Subsequent behavioral testing is performed three days after therapy injection and then weekly thereafter confirming that neuropathic pain does not return after treatment. The antibody dose response curve has been generated and confirmed the treatment dose range.

Cognition Dependent Anxiety-Like and Depression-Like Behavioral Tests

The cognitive dependent anxiety and depression tests are performed once in weeks 6-8 after model induction. Anxiety-like behaviors are quantified with the light/dark test and elevated Plus Maze. Depression is assessed with the sucrose splash test.

Light/Dark Place Preference: The light/dark box used to assess anxiety related behaviors consists of two equally sized chambers, one darkened and one brightly illuminated with a standard 53W, 120V GE white light bulb (890 Lumen, 75.7 W/m2). Each mouse is placed into the dark side of the test box facing away from the light side immediately after exposure to a mild, recorded acoustic startle disturbance (2 min). The mice have free access to either chamber (10 cm×10 cm) separated by a 3 cm×3 cm door. Quantified behaviors monitored by computer linked video recording are (1) time spent in each chamber, (2) number of transitions between chambers, (3) number of rearing events, (4) entry latency into the light chamber, and (5) latency of first re-entry (transition) back into the dark chamber. The light/dark test is conducted in postoperative week 6.

Elevated Plus Maze with two arms open and two arms closed: The elevated plus maze is a widely used test for measuring anxiety-like behavior, by determining a preference between a comparatively safe environment (closed arms) and a threatening environment (open arms). In principle, the more "anxious" the subjects are, the less likely they will explore a risky or threatening environment. The animal is placed in the center of the elevated four-arm maze for five minutes of isolated video recording. Fear/anxiety-like behavior is determined by the number of open and closed arm entries, total open and closed arm occupancy, and by the number of exploratory rearing events. High anxiety states are directly related to open arm avoidance. The maze is disinfected between each animal testing.

Splash Test for Depression using 10% sucrose: The splash test allows measurement of decreased grooming behavior as a symptom of depression. This index is affected by chronic mild stress and corrected by chronic antidepressant treatment. Frequency, duration, and latency of grooming are scored (10 minutes) after spraying a 10% sucrose solution on the dorsal coat (~250 µl near base of tail) by observers blinded to treatment group.

Novel Object Recognition (NOR) Learning Test

Any alteration in cognition is determined with the novel object recognition test. During training, mice are acclimated individually to a clear plastic cage with open top (56 cm×30 cm×20 cm) for one hour before two identical DUPLO minifigures (Lego A/S, Billund, Denmark) are placed in opposite corners of the cage for five minutes. On the testing day, animals are again acclimated to the clear cage for one hour prior to placing the two identical mini-figures in the same positions of the cage for five minutes, before returning to the home cage. Four hours later the animal is returned to the test cage and one original figure is replaced with a novel object and time spent exploring the objects recorded. The reported Recognition Index (RI) is calculated as the percent time spent exploring the novel object of total object exploration time.

Neuropathology/Quantitative Immunohistology

Mice are euthanized and perfused transcardially with buffered paraformaldehyde (4%). Quantitative immunohistology using computer assisted Fluorescence Microscopy analysis in mice indicates CCK-B receptor is localized in TG, brainstem, and limbic structures, and the relationship to neurons and glial. Analysis of immunostaining in pain pathway anatomical structures is done in a minimum of four sections/region/animal to obtain mean staining intensities±standard error of the mean (SEM) for group comparisons. Dual immunostaining of neurons (NeuN) and differentiating biomarkers specific for glial cells (GFAP, Iba1) identify cellular pattern shifts along with the biodistribution of CCK-B receptor and scFv antibodies in TG and limbic brain regions. We will also determine the ability of the CCK-B receptor antibody treatment to reduce the pathological increases in mitochondrial stress proteins and hyperphosphorylated tau (pS396/S404 tau).

The complete disclosure of all patents, patent applications, and publications, and electronically available material (including, for instance, nucleotide sequence submissions in, e.g., GenBank and RefSeq, and amino acid sequence submissions in, e.g., SwissProt, PIR, PRF, PDB, and translations from annotated coding regions in GenBank and RefSeq) cited herein are incorporated by reference in their entirety. In the event that any inconsistency exists between the disclosure of the present application and the disclosure(s) of any document incorporated herein by reference, the disclosure of the present application shall govern. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

Unless otherwise indicated, all numbers expressing quantities of components, molecular weights, and so forth used in the specification and claims are to be understood as being modified in all instances by the term "about." Accordingly, unless otherwise indicated to the contrary, the numerical parameters set forth in the specification and claims are approximations that may vary depending upon the desired properties sought to be obtained by the present invention. At the very least, and not as an attempt to limit the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. All numerical values, however, inherently contain a range necessarily resulting from the standard deviation found in their respective testing measurements.

All headings are for the convenience of the reader and should not be used to limit the meaning of the text that follows the heading, unless so specified.

```
                        Sequence Listing Free Text

SEQ ID NO: 1
FDGDSDSDSQ SRVRNQ

SEQ ID NO: 2
CETPRIRGTG TRELE

SEQ ID NO: 3 - CCK-BR-scFv77-2
MAGAELVRSG ASVKLSCTAS GFNIKDYYIH WVKQRPEQGL EWIGWIDPEN GDTEYAPKFQ
GKATMTADTS SNTAYLQLSS LTSEDTAVYY CNAGGRFAYW GQGTLVTVSA AKTTAPSGGG
GSGGGGSGGG GGSGGGGSSS LSVSAGEKVT MSCKSSQSLL NSGNQKNYLA WYQQKPGQPP
KLLIYGASTR ESGVPDRFTG SGSGTDFTLT ISSVQAEDLA VYYCQNDHSY PYTFGGGTKL
EIKRADAAAL E

SEQ ID NO: 4 - CCK-BR-scFv14-3
MAGAELVRSG ASVKLSCTAS GFNIKDYYIH WVKQRPEQGL EWIGWIDPEN GDTEYAPKFQ
GKATMTADTS SNTAYLQLSS LTSEDTAVYY CNAGGRFAYW GQGTLVTVSA AKTTAPSGGG
GSGGGGSGGG GGSGGGGSSS LSVSSGEKVT MSCKSSQSLL NSGNQKNYLA WYQQKPGQPP
KLLIYWASTD ESGVPDRFTG SGSGTDFTLT VSSVQAENLA LYYCQNDHSY PYHVFDGGTK
LEIKRADAAA LE

SEQ ID NO: 5 - CCK-BR-scFv134-1
MAGAELVKPG ASVKMSCKAS GYTFTDYWMH WVKQRPGQGL EWIGAIDTSD SYTSYNQKFK
GKATLTVDKS SSTAYIQLSS LTSEDSAVYY CARSEGYLPF DYWGQGTTLT VSSAKTTAPS
GGGGSGGGGS GGGGSGGGG SLSLPVSFGD QVSISCRSSQ SLANSYGNTY LSWYLHKPGQ
SPQLLIYGIS NRFSGVPDRF SGSGSGTDFT LKISTIKPED LGMYYCLQGT HQPRTFGGGT
KLEIKRADAA ALE

SEQ ID NO: 6 - CCKBR-scFv8-3
MAQVQLKESG AELAKPGASV KMSCKASGYT FTSYWMHWVK QRPGQGLEWI GYINPSTGYT
EYNQKFKDKA TLTADKSSST AYMQLSSLTS EDSAVYYCAR DYGSSFDYWG QGTTLTVSSG
GGGSGGGGSG GGGGSGGGGS LTLSVTIGQP ASISCKSSQS LLDSGNQKNY LAWYQQKPGQ
PPKLLIYGAS TRESGVPDRF TGSGSGTDFT LTISSVQAED LAVYYCQNDH SYPYTFGGGT
KLEIKRADAA ALE
```

Sequence Listing Free Text

```
SEQ ID NO: 7 - CCKBR-scFv93-1
MAQVQLKESG PGXVAPSQSL SITCTVSGFS LTSYGVHWVR QPPGKGLEWL GVIWAGGSTN
YNSALMSRLS ISKDNSKSQV FLKMNSLQTD DTAMYYCARG LRGAMDYWGQ GTSVTVSSGG
GGGSGGGGSSS LSVSAGEKVT MSCKSSQSLL ASGNQNNYLA WHQQKPGRSP KMLIIWASTR
ESGVPDRFTG SGSGTDFTLT ISSVQAEDVA VYYCQNDHSY PFTFGSGTKL EIKRADAAAL
E

SEQ ID NO: 8 - CCKBR-scFv11-2
MAQVQLKQSG AELVRPGSSV KISCKASGYA FTNYLIEWVK QRPGQGLEWI GQIYPGDGDT
NYNGKFKGKA TLTVDNSSST AYMELRSLTS EDSAVYYCAR AATWYYAMDY WGQGTSVTVS
SGGGGSGGGG SAIMSASPGE KVTITCSASS SVSYMHWFQQ KPGTSPKLWI YSTSNLASGV
PARFSGSGSG TSYSLTISSM EAEDAASYFC HQWSSYPWTF GGGTKLEIKR ADAAALE

SEQ ID NO: 9 - CCKBR-scFv26-1
MAGAELVRSG ASVKLSCTAS GFNIKDYYIH WVKQRPEQGL EWIGWIDPEN GDTEYAPKFQ
GKATMTADTS SNTAYLQLSS LTSEDTAVYY CNAGGRFAYW GQGTLVTVSA AKTTAPSGGG
GSGGGGSGGG GGSGGGGSSS LSVSSGEKVT MSCKSSQSLL NSGNQKNYLA WYQQKPGQPP
KLLIYWASTD ESGVPDRFTG SGSGTDFTLT VSSVQAENLA LYYCQNDHSY PYTFGGGTKL
EIKRADAAAL E

SEQ ID NO: 10 - CCKBR-scFv28-1
MAGAELVRSG ASVKLSCTAS GFNIKDYYIH WVKQRPEQGL EWIGWIDPEN GDTEYAPKFQ
GKATMTADTS SNTAYLQLSS LTSEDTAVYY CNAGGRFAYW GQGTLVTVSA AKTTAPSGGG
GSGGGGSGGG GGSGGGGSSS LSVSSGEKVT MSCKSSQSLL NSGNQKNYLA WYQQKPGQPP
KLLIYWASTD ESGVPDRFTG SGSGTDFTLT VSSVQAENLA LYYCQNDHSY PYHVFDGGTK
LEIKRADAAA LE

SEQ ID NO: 11 - MVH_F1
GCGAATTCCA CCATGGCCGA KGTRMAGCTT CAGGAGTC

SEQ ID NO: 12 - MVH_F2
GCGAATTCCA CCATGGCCGA GGTBCAGCTB CAGCAGTC

SEQ ID NO: 13 - MVH_F3
GCGAATTCCA CCATGGCCCA GGTGCAGCTG AAGSASTC

SEQ ID NO: 14 - MVH_F4
GCGAATTCCA CCATGGCCGA GGTCCARCTG CAACARTC

SEQ ID NO: 15 - MVH_F5
GCGAATTCCA CCATGGCCCA GGTYCAGCTB CAGCARTC

SEQ ID NO: 16 - MVH_F6
GCGAATTCCA CCATGGCCCA GGTYCARCTG CAGCAGTC

SEQ ID NO: 17 - MVH_F7
GCGAATTCCA CCATGGCCCA GGTCCAGGTG AAGCAGTC

SEQ ID NO: 18 - MVH_F8
GCGAATTCCA CCATGGCCGA GGTGAASSTG GTGGAATC

SEQ ID NO: 19 - MVH_F9
GCGAATTCCA CCATGGCCGA VGTGAWGYTG GTGGAGTC

SEQ ID NO: 20 - MVH_F10
GCGAATTCCA CCATGGCCGA GGTGCAGSKG GTGGAGTC

SEQ ID NO: 21 - MVH_F11
GCGAATTCCA CCATGGCCGA KGTGCAMCTG GTGGAGTC

SEQ ID NO: 22 - MVH_F12
GCGAATTCCA CCATGGCCGA GGTGAAGCTG ATGGARTC

SEQ ID NO: 23 - MVH_F13
GCGAATTCCA CCATGGCCGA GGTGCARCTT GTTGAGTC

SEQ ID NO: 24 - MVH_F14
GCGAATTCCA CCATGGCCGA RGTRAAGCTT CTCGAGTC

SEQ ID NO: 25 - MVH_F15
GCGAATTCCA CCATGGCCGA AGTGAARSTT GAGGAGTC

SEQ ID NO: 26 - MVH_F16
GCGAATTCCA CCATGGCCCA GGTTACTCTR AAAGWGTSTG
```

| Sequence Listing Free Text |
|---|

SEQ ID NO: 27 - MVH_F17
GCGAATTCCA CCATGGCCCA GGTCCAACTV CAGCARCC

SEQ ID NO: 28 - MVH_F18
GCGAATTCCA CCATGGCCGA TGTGAACTTG GAAGTGTC

SEQ ID NO: 29 - MVH_F19
GCGAATTCCA CCATGGCCGA GGTGAAGGTC ATCGAGTC

SEQ ID NO: 30 MVH_F20
GCGAATTCCA CCATGGCCGG GGCAGAGCTT GTGAAGCCA

SEQ ID NO: 31 - MVH_F21
GCGAATTCCA CCATGGCCGG AGGAGGCTTG ATGCAACCT

SEQ ID NO: 32 - MVH_F22
GCGAATTCCA CCATGGCCGG ACCTGAGCTG GAGATGCCT

SEQ ID NO: 33 - MVH_F23
GCGAATTCCA CCATGGCCGG ACCTGGCCTG GTGAGACCT

SEQ ID NO: 34 - MVH_F24
GCGAATTCCA CCATGGCCGG GGGAGGCTTA GTGAAGCCT

SEQ ID NO: 35 - MVH_F25
GCGAATTCCA CCATGGCCGG GGCAGAGCTT GTGAAGCCA

SEQ ID NO: 36 - MVH_F26
GCGAATTCCA CCATGGCCGG AGGGGCTTG GTACAGCCT

SEQ ID NO: 37 - MVH_F27
GCGAATTCCA CCATGGCCGG GGCAGAGCTT GTGAGGTCA

SEQ ID NO: 38 - MVH_R1
GGAGCCGCCG CCGCCGCCAG AACCACCACC ACC_GGATCC_A CCACCACCCG AGGAAACGGT
GACCGTGGT

SEQ ID NO: 39 - MVH_R2
GGAGCCGCCG CCGCCGCCAG AACCACCACC ACC_GGATCC_A CCACCACCCG AGGAGACTGT
GAGAGTGGT

SEQ ID NO: 40 - MVH_R3
GGAGCCGCCG CCGCCGCCAG AACCACCACC ACC_GGATCC_A CCACCACCCG CAGAGACAGT
GACCAGAGT

SEQ ID NO: 41 - MVH_R4
GGAGCCGCCG CCGCCGCCAG AACCACCACC ACC_GGATCC_A CCACCACCCG AGGAGACGGT
GACTGAGGT

SEQ ID NO: 42 - MVH_R5
GGAGCCGCCG CCGCCGCCAG AACCACCACC ACC_GGATCC_A CCACCACCCG ATGGGCTGT
TGTTTTGGC

SEQ ID NO: 43 - MVH_R6
GGAGCCGCCG CCGCCGCCAG AACCACCACC ACC_GGATCC_A CCACCACCTG ATGGGGGTGT
TGTTTTGGC

SEQ ID NO: 44 - MVH_R7
GGAGCCGCCG CCGCCGCCAG AACCACCACC ACC_GGATCC_A CCACCACCCG ATGGGCTGT
TGTTTTGGC

SEQ ID NO: 45 - MVH_R8
GGAGCCGCCG CCGCCGCCAG AACCACCACC ACC_GGATCC_A CCACCACCCG ATGGGCTGT
TGTTTTGGC

SEQ ID NO: 46 - MVH_R9
GGAGCCGCCG CCGCCGCCAG AACCACCACC ACC_GGATCC_A CCACCACCCG ATGGGCTGT
TGTTTTGGC

SEQ ID NO: 47 - MVH_R10
GGAGCCGCCG CCGCCGCCAG AACCACCACC ACC_GGATCC_A CCACCACCCG ATGGGCTGT
TGTTTTGGC

SEQ ID NO: 48 - MVH_R11
GGAGCCGCCG CCGCCGCCAG AACCACCACC ACC_GGATCC_A CCACCACCAG ATGGGGGTGT
CGTTTTGGC

Sequence Listing Free Text

SEQ ID NO: 49 - MVH_R12
GGAGCCGCCG CCGCCGCCAG AACCACCACC ACCGGATCCA CCACCACCCG ATGGGGCTGT
TGTTTTGGC

SEQ ID NO: 50 - MVK_F1
GGCGGCGGCG GCTCCGGTGG TGGTGGATCC GCAATCATGT CTGCATCTCC

SEQ ID NO: 51 - MVK_F2
GGCGGCGGCG GCTCCGGTGG TGGTGGATCC GCCTCCCTAT CTGTATCTGT G

SEQ ID NO: 52 - MVK_F3
GGCGGCGGCG GCTCCGGTGG TGGTGGATCC GCCTCCCTAT CTGCATCTGT G

SEQ ID NO: 53 - MVK_F4
GGCGGCGGCG GCTCCGGTGG TGGTGGATCC CTCACTTTGT CGGTTACCAT T

SEQ ID NO: 54 - MVK_F5
GGCGGCGGCG GCTCCGGTGG TGGTGGATCC TCAGCCTCTT TCTCCCTGGG A

SEQ ID NO: 55 - MVK_F6
GGCGGCGGCG GCTCCGGTGG TGGTGGATCC TCCTCCCTGA GTGTGTCAGC A

SEQ ID NO: 56 - MVK_F7
GGCGGCGGCG GCTCCGGTGG TGGTGGATCC CTCTCCCTGC CTGTCAGTCT T

SEQ ID NO: 57 - MVK_F8
GGCGGCGGCG GCTCCGGTGG TGGTGGATCC CTCTCCCTGC CTGTCAGTCT T

SEQ ID NO: 58 - MVK_R
AGTGCGGCCG CATCAGCCCG TTTTATTTCC AA

SEQ ID NO: 59 - RDT7
CTATAGAAGG GTAATACGAC TCACTATAGG GCGAATTCCA CCATGGCC

What is claimed is:

1. A pharmaceutical composition comprising:
an antibody, or fragment thereof, that specifically binds to a target peptide that mediates pain in a subject; and a pharmaceutically acceptable carrier, wherein the antibody comprises at least one of SEQ ID NOs:3-10.

2. The pharmaceutical composition of claim 1, wherein the antibody is a scFv.

3. The pharmaceutical composition of claim 1, wherein the composition relieves acute orofacial pain.

4. The pharmaceutical composition of claim 1, wherein the composition relieves chronic orofacial pain.

5. The pharmaceutical composition of claim 1, wherein the composition reduces anxiety-related behaviors.

6. The pharmaceutical composition of claim 1, wherein the antibody comprises a fluorescent tag.

7. The pharmaceutical composition of claim 6, wherein the fluorescent tag comprises monomeric red fluorescent protein (RFP1).

8. The pharmaceutical composition of claim 1, wherein the antibody comprises an affinity tag.

9. The pharmaceutical composition of claim 8, wherein the affinity tag comprises a 6×His tag.

10. The pharmaceutical composition of claim 1, wherein the antibody comprises at least one of SEQ ID NOs:3-5.

11. A method for relieving pain, the method comprising administering to a subject experiencing pain a sufficient amount of the composition of claim 1 to alleviate the pain.

12. The method of claim 11, wherein the pain comprises orofacial pain.

13. The method of claim 12, wherein the orofacial pain is neuropathic.

* * * * *

SEQUENCE LISTING

<160> NUMBER OF SEQ ID NOS: 59

<210> SEQ ID NO 1
<211> LENGTH: 16
<212> TYPE: PRT
<213> ORGANISM: Homo sapiens

<400> SEQUENCE: 1

Phe Asp Gly Asp Ser Asp Ser Asp Ser Gln Ser Arg Val Arg Asn Gln
1               5                   10                  15

<210> SEQ ID NO 2
<211> LENGTH: 15
<212> TYPE: PRT
<213> ORGANISM: Homo sapiens

<400> SEQUENCE: 2

Cys Glu Thr Pro Arg Ile Arg Gly Thr Gly Thr Arg Glu Leu Glu
1               5                   10                  15

<210> SEQ ID NO 3
<211> LENGTH: 251
<212> TYPE: PRT
<213> ORGANISM: Mus musculus

<400> SEQUENCE: 3

Met Ala Gly Ala Glu Leu Val Arg Ser Gly Ala Ser Val Lys Leu Ser
1               5                   10                  15

Cys Thr Ala Ser Gly Phe Asn Ile Lys Asp Tyr Tyr Ile His Trp Val
                20                  25                  30

Lys Gln Arg Pro Glu Gln Gly Leu Glu Trp Ile Gly Trp Ile Asp Pro
             35                  40                  45

Glu Asn Gly Asp Thr Glu Tyr Ala Pro Lys Phe Gln Gly Lys Ala Thr
 50                  55                  60

Met Thr Ala Asp Thr Ser Ser Asn Thr Ala Tyr Leu Gln Leu Ser Ser
 65                  70                  75                  80

Leu Thr Ser Glu Asp Thr Ala Val Tyr Tyr Cys Asn Ala Gly Gly Arg
                 85                  90                  95

Phe Ala Tyr Trp Gly Gln Gly Thr Leu Val Thr Val Ser Ala Ala Lys
            100                 105                 110

Thr Thr Ala Pro Ser Gly Gly Gly Gly Ser Gly Gly Gly Gly Ser Gly
            115                 120                 125

Gly Gly Gly Ser Gly Gly Gly Gly Ser Ser Ser Leu Ser Val Ser
        130                 135                 140

Ala Gly Glu Lys Val Thr Met Ser Cys Lys Ser Ser Gln Ser Leu Leu
145                 150                 155                 160

Asn Ser Gly Asn Gln Lys Asn Tyr Leu Ala Trp Tyr Gln Gln Lys Pro
                165                 170                 175

Gly Gln Pro Pro Lys Leu Leu Ile Tyr Gly Ala Ser Thr Arg Glu Ser
            180                 185                 190

Gly Val Pro Asp Arg Phe Thr Gly Ser Gly Ser Gly Thr Asp Phe Thr
        195                 200                 205

Leu Thr Ile Ser Ser Val Gln Ala Glu Asp Leu Ala Val Tyr Tyr Cys
    210                 215                 220

Gln Asn Asp His Ser Tyr Pro Tyr Thr Phe Gly Gly Thr Lys Leu
225                 230                 235                 240

Glu Ile Lys Arg Ala Asp Ala Ala Ala Leu Glu
            245                 250

<210> SEQ ID NO 4
<211> LENGTH: 252
<212> TYPE: PRT
<213> ORGANISM: Mus musculus

<400> SEQUENCE: 4

Met Ala Gly Ala Glu Leu Val Arg Ser Gly Ala Ser Val Lys Leu Ser
 1               5                  10                  15

Cys Thr Ala Ser Gly Phe Asn Ile Lys Asp Tyr Tyr Ile His Trp Val
             20                  25                  30

Lys Gln Arg Pro Glu Gln Gly Leu Glu Trp Ile Gly Trp Ile Asp Pro
             35                  40                  45

Glu Asn Gly Asp Thr Glu Tyr Ala Pro Lys Phe Gln Gly Lys Ala Thr
 50                  55                  60

Met Thr Ala Asp Thr Ser Ser Asn Thr Ala Tyr Leu Gln Leu Ser Ser
 65                  70                  75                  80

Leu Thr Ser Glu Asp Thr Ala Val Tyr Tyr Cys Asn Ala Gly Gly Arg
                 85                  90                  95

Phe Ala Tyr Trp Gly Gln Gly Thr Leu Val Thr Val Ser Ala Ala Lys
            100                 105                 110

Thr Thr Ala Pro Ser Gly Gly Gly Gly Ser Gly Gly Gly Gly Ser Gly
            115                 120                 125

Gly Gly Gly Ser Gly Gly Gly Gly Ser Ser Ser Leu Ser Val Ser
        130                 135                 140

Ser Gly Glu Lys Val Thr Met Ser Cys Lys Ser Ser Gln Ser Leu Leu 145                 150                 155                 160
Asn Ser Gly Asn Gln Lys Asn Tyr Leu Ala Trp Tyr Gln Gln Lys Pro
                    165                 170                 175

Gly Gln Pro Pro Lys Leu Leu Ile Tyr Trp Ala Ser Thr Asp Glu Ser
            180                 185                 190

Gly Val Pro Asp Arg Phe Thr Gly Ser Gly Ser Gly Thr Asp Phe Thr
            195                 200                 205

Leu Thr Val Ser Ser Val Gln Ala Glu Asn Leu Ala Leu Tyr Tyr Cys
    210                 215                 220

Gln Asn Asp His Ser Tyr Pro Tyr His Val Phe Asp Gly Gly Thr Lys
225                 230                 235                 240

Leu Glu Ile Lys Arg Ala Asp Ala Ala Leu Glu
                245                 250

<210> SEQ ID NO 5
<211> LENGTH: 253
<212> TYPE: PRT
<213> ORGANISM: Mus musculus

<400> SEQUENCE: 5

Met Ala Gly Ala Glu Leu Val Lys Pro Gly Ala Ser Val Lys Met Ser
1               5                   10                  15

Cys Lys Ala Ser Gly Tyr Thr Phe Thr Asp Tyr Trp Met His Trp Val
            20                  25                  30

Lys Gln Arg Pro Gly Gln Gly Leu Glu Trp Ile Gly Ala Ile Asp Thr
        35                  40                  45

Ser Asp Ser Tyr Thr Ser Tyr Asn Gln Lys Phe Lys Gly Lys Ala Thr
    50                  55                  60

Leu Thr Val Asp Lys Ser Ser Ser Thr Ala Tyr Ile Gln Leu Ser Ser
65                  70                  75                  80

Leu Thr Ser Glu Asp Ser Ala Val Tyr Tyr Cys Ala Arg Ser Glu Gly
                85                  90                  95

Tyr Leu Pro Phe Asp Tyr Trp Gly Gln Gly Thr Thr Leu Thr Val Ser
            100                 105                 110

Ser Ala Lys Thr Thr Ala Pro Ser Gly Gly Gly Ser Gly Gly Gly
        115                 120                 125

Gly Ser Gly Gly Gly Gly Ser Gly Gly Gly Ser Leu Ser Leu
    130                 135                 140

Pro Val Ser Phe Gly Asp Gln Val Ser Ile Ser Cys Arg Ser Ser Gln
145                 150                 155                 160

Ser Leu Ala Asn Ser Tyr Gly Asn Thr Tyr Leu Ser Trp Tyr Leu His
                165                 170                 175

Lys Pro Gly Gln Ser Pro Gln Leu Leu Ile Tyr Gly Ile Ser Asn Arg
            180                 185                 190

Phe Ser Gly Val Pro Asp Arg Phe Ser Gly Ser Gly Ser Gly Thr Asp
        195                 200                 205

Phe Thr Leu Lys Ile Ser Thr Ile Lys Pro Glu Asp Leu Gly Met Tyr
    210                 215                 220

Tyr Cys Leu Gln Gly Thr His Gln Pro Arg Thr Phe Gly Gly Gly Thr
225                 230                 235                 240

Lys Leu Glu Ile Lys Arg Ala Asp Ala Ala Leu Glu
                245                 250

<210> SEQ ID NO 6
<211> LENGTH: 253

<212> TYPE: PRT
<213> ORGANISM: Mus musculus

<400> SEQUENCE: 6

```
Met Ala Gln Val Gln Leu Lys Glu Ser Gly Ala Glu Leu Ala Lys Pro
1               5                   10                  15

Gly Ala Ser Val Lys Met Ser Cys Lys Ala Ser Gly Tyr Thr Phe Thr
                20                  25                  30

Ser Tyr Trp Met His Trp Val Lys Gln Arg Pro Gly Gln Gly Leu Glu
            35                  40                  45

Trp Ile Gly Tyr Ile Asn Pro Ser Thr Gly Tyr Thr Glu Tyr Asn Gln
        50                  55                  60

Lys Phe Lys Asp Lys Ala Thr Leu Thr Ala Asp Lys Ser Ser Ser Thr
65                  70                  75                  80

Ala Tyr Met Gln Leu Ser Ser Leu Thr Ser Glu Asp Ser Ala Val Tyr
                85                  90                  95

Tyr Cys Ala Arg Asp Tyr Gly Ser Ser Phe Asp Tyr Trp Gly Gln Gly
            100                 105                 110

Thr Thr Leu Thr Val Ser Ser Gly Gly Gly Ser Gly Gly Gly Gly
        115                 120                 125

Ser Gly Gly Gly Gly Ser Gly Gly Gly Ser Leu Thr Leu Ser
    130                 135                 140

Val Thr Ile Gly Gln Pro Ala Ser Ile Ser Cys Lys Ser Ser Gln Ser
145                 150                 155                 160

Leu Leu Asp Ser Gly Asn Gln Lys Asn Tyr Leu Ala Trp Tyr Gln Gln
                165                 170                 175

Lys Pro Gly Gln Pro Pro Lys Leu Leu Ile Tyr Gly Ala Ser Thr Arg
            180                 185                 190

Glu Ser Gly Val Pro Asp Arg Phe Thr Gly Ser Gly Ser Gly Thr Asp
        195                 200                 205

Phe Thr Leu Thr Ile Ser Ser Val Gln Ala Glu Asp Leu Ala Val Tyr
    210                 215                 220

Tyr Cys Gln Asn Asp His Ser Tyr Pro Tyr Thr Phe Gly Gly Gly Thr
225                 230                 235                 240

Lys Leu Glu Ile Lys Arg Ala Asp Ala Ala Leu Glu
                245                 250
```

<210> SEQ ID NO 7
<211> LENGTH: 241
<212> TYPE: PRT
<213> ORGANISM: Mus musculus
<220> FEATURE:
<221> NAME/KEY: misc_feature
<222> LOCATION: (13)..(13)
<223> OTHER INFORMATION: Xaa can be any naturally occurring amino acid

<400> SEQUENCE: 7

```
Met Ala Gln Val Gln Leu Lys Glu Ser Gly Pro Gly Xaa Val Ala Pro
1               5                   10                  15

Ser Gln Ser Leu Ser Ile Thr Cys Thr Val Ser Gly Phe Ser Leu Thr
                20                  25                  30

Ser Tyr Gly Val His Trp Val Arg Gln Pro Pro Gly Lys Gly Leu Glu
            35                  40                  45

Trp Leu Gly Val Ile Trp Ala Gly Gly Ser Thr Asn Tyr Asn Ser Ala
        50                  55                  60

Leu Met Ser Arg Leu Ser Ile Ser Lys Asp Asn Ser Lys Ser Gln Val
65                  70                  75                  80
```

```
Phe Leu Lys Met Asn Ser Leu Gln Thr Asp Asp Thr Ala Met Tyr Tyr
                85                  90                  95
Cys Ala Arg Gly Leu Arg Gly Ala Met Asp Tyr Trp Gly Gln Gly Thr
            100                 105                 110
Ser Val Thr Val Ser Ser Gly Gly Gly Ser Gly Gly Gly Gly Ser
        115                 120                 125
Ser Ser Leu Ser Val Ser Ala Gly Glu Lys Val Thr Met Ser Cys Lys
130                 135                 140
Ser Ser Gln Ser Leu Leu Ala Ser Gly Asn Gln Asn Asn Tyr Leu Ala
145                 150                 155                 160
Trp His Gln Gln Lys Pro Gly Arg Ser Pro Lys Met Leu Ile Ile Trp
                165                 170                 175
Ala Ser Thr Arg Glu Ser Gly Val Pro Asp Arg Phe Thr Gly Ser Gly
            180                 185                 190
Ser Gly Thr Asp Phe Thr Leu Thr Ile Ser Ser Val Gln Ala Glu Asp
        195                 200                 205
Val Ala Val Tyr Tyr Cys Gln Asn Asp His Ser Tyr Pro Phe Thr Phe
210                 215                 220
Gly Ser Gly Thr Lys Leu Glu Ile Lys Arg Ala Asp Ala Ala Ala Leu
225                 230                 235                 240
Glu

<210> SEQ ID NO 8
<211> LENGTH: 237
<212> TYPE: PRT
<213> ORGANISM: Mus musculus

<400> SEQUENCE: 8

Met Ala Gln Val Gln Leu Lys Gln Ser Gly Ala Glu Leu Val Arg Pro
1               5                   10                  15
Gly Ser Ser Val Lys Ile Ser Cys Lys Ala Ser Gly Tyr Ala Phe Thr
            20                  25                  30
Asn Tyr Leu Ile Glu Trp Val Lys Gln Arg Pro Gly Gln Gly Leu Glu
        35                  40                  45
Trp Ile Gly Gln Ile Tyr Pro Gly Asp Gly Asp Thr Asn Tyr Asn Gly
    50                  55                  60
Lys Phe Lys Gly Lys Ala Thr Leu Thr Val Asp Asn Ser Ser Ser Thr
65                  70                  75                  80
Ala Tyr Met Glu Leu Arg Ser Leu Thr Ser Glu Asp Ser Ala Val Tyr
                85                  90                  95
Tyr Cys Ala Arg Ala Ala Thr Trp Tyr Tyr Ala Met Asp Tyr Trp Gly
            100                 105                 110
Gln Gly Thr Ser Val Thr Val Ser Ser Gly Gly Gly Ser Gly Gly
        115                 120                 125
Gly Gly Ser Ala Ile Met Ser Ala Ser Pro Gly Glu Lys Val Thr Ile
130                 135                 140
Thr Cys Ser Ala Ser Ser Ser Val Ser Tyr Met His Trp Phe Gln Gln
145                 150                 155                 160
Lys Pro Gly Thr Ser Pro Lys Leu Trp Ile Tyr Ser Thr Ser Asn Leu
                165                 170                 175
Ala Ser Gly Val Pro Ala Arg Phe Ser Gly Ser Gly Ser Gly Thr Ser
            180                 185                 190
Tyr Ser Leu Thr Ile Ser Ser Met Glu Ala Glu Asp Ala Ala Ser Tyr
        195                 200                 205
```

Phe Cys His Gln Trp Ser Ser Tyr Pro Trp Thr Phe Gly Gly Gly Thr
    210                 215                 220

Lys Leu Glu Ile Lys Arg Ala Asp Ala Ala Ala Leu Glu
225                 230                 235

<210> SEQ ID NO 9
<211> LENGTH: 251
<212> TYPE: PRT
<213> ORGANISM: Mus musculus

<400> SEQUENCE: 9

Met Ala Gly Ala Glu Leu Val Arg Ser Gly Ala Ser Val Lys Leu Ser
1               5                   10                  15

Cys Thr Ala Ser Gly Phe Asn Ile Lys Asp Tyr Tyr Ile His Trp Val
            20                  25                  30

Lys Gln Arg Pro Glu Gln Gly Leu Glu Trp Ile Gly Trp Ile Asp Pro
        35                  40                  45

Glu Asn Gly Asp Thr Glu Tyr Ala Pro Lys Phe Gln Gly Lys Ala Thr
    50                  55                  60

Met Thr Ala Asp Thr Ser Ser Asn Thr Ala Tyr Leu Gln Leu Ser Ser
65                  70                  75                  80

Leu Thr Ser Glu Asp Thr Ala Val Tyr Tyr Cys Asn Ala Gly Gly Arg
                85                  90                  95

Phe Ala Tyr Trp Gly Gln Gly Thr Leu Val Thr Val Ser Ala Ala Lys
            100                 105                 110

Thr Thr Ala Pro Ser Gly Gly Gly Gly Ser Gly Gly Gly Gly Ser Gly
        115                 120                 125

Gly Gly Gly Ser Gly Gly Gly Gly Ser Ser Ser Leu Ser Val Ser
    130                 135                 140

Ser Gly Glu Lys Val Thr Met Ser Cys Lys Ser Ser Gln Ser Leu Leu
145                 150                 155                 160

Asn Ser Gly Asn Gln Lys Asn Tyr Leu Ala Trp Tyr Gln Gln Lys Pro
                165                 170                 175

Gly Gln Pro Pro Lys Leu Leu Ile Tyr Trp Ala Ser Thr Asp Glu Ser
            180                 185                 190

Gly Val Pro Asp Arg Phe Thr Gly Ser Gly Ser Gly Thr Asp Phe Thr
        195                 200                 205

Leu Thr Val Ser Ser Val Gln Ala Glu Asn Leu Ala Leu Tyr Tyr Cys
    210                 215                 220

Gln Asn Asp His Ser Tyr Pro Tyr Thr Phe Gly Gly Gly Thr Lys Leu
225                 230                 235                 240

Glu Ile Lys Arg Ala Asp Ala Ala Ala Leu Glu
                245                 250

<210> SEQ ID NO 10
<211> LENGTH: 252
<212> TYPE: PRT
<213> ORGANISM: Mus musculus

<400> SEQUENCE: 10

Met Ala Gly Ala Glu Leu Val Arg Ser Gly Ala Ser Val Lys Leu Ser
1               5                   10                  15

Cys Thr Ala Ser Gly Phe Asn Ile Lys Asp Tyr Tyr Ile His Trp Val
            20                  25                  30

Lys Gln Arg Pro Glu Gln Gly Leu Glu Trp Ile Gly Trp Ile Asp Pro
        35                  40                  45

Glu Asn Gly Asp Thr Glu Tyr Ala Pro Lys Phe Gln Gly Lys Ala Thr
 50                  55                  60

Met Thr Ala Asp Thr Ser Ser Asn Thr Ala Tyr Leu Gln Leu Ser Ser
 65                  70                  75                  80

Leu Thr Ser Glu Asp Thr Ala Val Tyr Tyr Cys Asn Ala Gly Gly Arg
                 85                  90                  95

Phe Ala Tyr Trp Gly Gln Gly Thr Leu Val Thr Val Ser Ala Ala Lys
                100                 105                 110

Thr Thr Ala Pro Ser Gly Gly Gly Ser Gly Gly Gly Ser Gly
            115                 120                 125

Gly Gly Gly Ser Gly Gly Gly Ser Ser Leu Ser Val Ser
        130                 135                 140

Ser Gly Glu Lys Val Thr Met Ser Cys Lys Ser Gln Ser Leu Leu
145                 150                 155                 160

Asn Ser Gly Asn Gln Lys Asn Tyr Leu Ala Trp Tyr Gln Gln Lys Pro
                165                 170                 175

Gly Gln Pro Pro Lys Leu Leu Ile Tyr Trp Ala Ser Thr Asp Glu Ser
            180                 185                 190

Gly Val Pro Asp Arg Phe Thr Gly Ser Gly Ser Gly Thr Asp Phe Thr
            195                 200                 205

Leu Thr Val Ser Ser Val Gln Ala Glu Asn Leu Ala Leu Tyr Tyr Cys
210                 215                 220

Gln Asn Asp His Ser Tyr Pro Tyr His Val Phe Asp Gly Gly Thr Lys
225                 230                 235                 240

Leu Glu Ile Lys Arg Ala Asp Ala Ala Ala Leu Glu
                245                 250

<210> SEQ ID NO 11
<211> LENGTH: 38
<212> TYPE: DNA
<213> ORGANISM: Artificial
<220> FEATURE:
<223> OTHER INFORMATION: Primer

<400> SEQUENCE: 11
gcgaattcca ccatggccga kgtrmagctt caggagtc                              38

<210> SEQ ID NO 12
<211> LENGTH: 38
<212> TYPE: DNA
<213> ORGANISM: Artificial
<220> FEATURE:
<223> OTHER INFORMATION: Primer

<400> SEQUENCE: 12
gcgaattcca ccatggccga ggtbcagctb cagcagtc                              38

<210> SEQ ID NO 13
<211> LENGTH: 38
<212> TYPE: DNA
<213> ORGANISM: Artificial
<220> FEATURE:
<223> OTHER INFORMATION: Primer

<400> SEQUENCE: 13
gcgaattcca ccatggccca ggtgcagctg aagsastc                              38

<210> SEQ ID NO 14
<211> LENGTH: 38

<212> TYPE: DNA
<213> ORGANISM: Artificial
<220> FEATURE:
<223> OTHER INFORMATION: Primer

<400> SEQUENCE: 14
gcgaattcca ccatggccga ggtccarctg caacartc        38

<210> SEQ ID NO 15
<211> LENGTH: 38
<212> TYPE: DNA
<213> ORGANISM: Artificial
<220> FEATURE:
<223> OTHER INFORMATION: Primer

<400> SEQUENCE: 15
gcgaattcca ccatggccca ggtycagctb cagcartc        38

<210> SEQ ID NO 16
<211> LENGTH: 38
<212> TYPE: DNA
<213> ORGANISM: Artificial
<220> FEATURE:
<223> OTHER INFORMATION: Primer

<400> SEQUENCE: 16
gcgaattcca ccatggccca ggtycarctg cagcagtc        38

<210> SEQ ID NO 17
<211> LENGTH: 38
<212> TYPE: DNA
<213> ORGANISM: Artificial
<220> FEATURE:
<223> OTHER INFORMATION: Primer

<400> SEQUENCE: 17
gcgaattcca ccatggccca ggtccaggtg aagcagtc        38

<210> SEQ ID NO 18
<211> LENGTH: 38
<212> TYPE: DNA
<213> ORGANISM: Artificial
<220> FEATURE:
<223> OTHER INFORMATION: Primer

<400> SEQUENCE: 18
gcgaattcca ccatggccga ggtgaasstg gtggaatc        38

<210> SEQ ID NO 19
<211> LENGTH: 38
<212> TYPE: DNA
<213> ORGANISM: Artificial
<220> FEATURE:
<223> OTHER INFORMATION: Primer

<400> SEQUENCE: 19
gcgaattcca ccatggccga vgtgawgytg gtggagtc        38

<210> SEQ ID NO 20
<211> LENGTH: 38
<212> TYPE: DNA
<213> ORGANISM: Artificial
<220> FEATURE:
<223> OTHER INFORMATION: Primer

<400> SEQUENCE: 20
gcgaattcca ccatggccga ggtgcagskg gtggagtc                38

<210> SEQ ID NO 21
<211> LENGTH: 38
<212> TYPE: DNA
<213> ORGANISM: Artificial
<220> FEATURE:
<223> OTHER INFORMATION: Primer

<400> SEQUENCE: 21
gcgaattcca ccatggccga kgtgcamctg gtggagtc                38

<210> SEQ ID NO 22
<211> LENGTH: 38
<212> TYPE: DNA
<213> ORGANISM: Artificial
<220> FEATURE:
<223> OTHER INFORMATION: Primer

<400> SEQUENCE: 22
gcgaattcca ccatggccga ggtgaagctg atggartc                38

<210> SEQ ID NO 23
<211> LENGTH: 38
<212> TYPE: DNA
<213> ORGANISM: Artificial
<220> FEATURE:
<223> OTHER INFORMATION: Primer

<400> SEQUENCE: 23
gcgaattcca ccatggccga ggtgcarctt gttgagtc                38

<210> SEQ ID NO 24
<211> LENGTH: 38
<212> TYPE: DNA
<213> ORGANISM: Artificial
<220> FEATURE:
<223> OTHER INFORMATION: Primer

<400> SEQUENCE: 24
gcgaattcca ccatggccga rgtraagctt ctcgagtc                38

<210> SEQ ID NO 25
<211> LENGTH: 38
<212> TYPE: DNA
<213> ORGANISM: Artificial
<220> FEATURE:
<223> OTHER INFORMATION: Primer

<400> SEQUENCE: 25
gcgaattcca ccatggccga agtgaarstt gaggagtc                38

<210> SEQ ID NO 26
<211> LENGTH: 40
<212> TYPE: DNA
<213> ORGANISM: Artificial
<220> FEATURE:
<223> OTHER INFORMATION: Primer

<400> SEQUENCE: 26
gcgaattcca ccatggccca ggttactctr aaagwgtstg              40

<210> SEQ ID NO 27
<211> LENGTH: 38
<212> TYPE: DNA
<213> ORGANISM: Artificial

```
<220> FEATURE:
<223> OTHER INFORMATION: Primer

<400> SEQUENCE: 27
gcgaattcca ccatggccca ggtccaactv cagcarcc                              38

<210> SEQ ID NO 28
<211> LENGTH: 38
<212> TYPE: DNA
<213> ORGANISM: Artificial
<220> FEATURE:
<223> OTHER INFORMATION: Primer

<400> SEQUENCE: 28
gcgaattcca ccatggccga tgtgaacttg gaagtgtc                              38

<210> SEQ ID NO 29
<211> LENGTH: 38
<212> TYPE: DNA
<213> ORGANISM: Artificial
<220> FEATURE:
<223> OTHER INFORMATION: Primer

<400> SEQUENCE: 29
gcgaattcca ccatggccga ggtgaaggtc atcgagtc                              38

<210> SEQ ID NO 30
<211> LENGTH: 39
<212> TYPE: DNA
<213> ORGANISM: Artificial
<220> FEATURE:
<223> OTHER INFORMATION: Primer

<400> SEQUENCE: 30
gcgaattcca ccatggccgg ggcagagctt gtgaagcca                             39

<210> SEQ ID NO 31
<211> LENGTH: 39
<212> TYPE: DNA
<213> ORGANISM: Artificial
<220> FEATURE:
<223> OTHER INFORMATION: Primer

<400> SEQUENCE: 31
gcgaattcca ccatggccgg aggaggcttg atgcaacct                             39

<210> SEQ ID NO 32
<211> LENGTH: 39
<212> TYPE: DNA
<213> ORGANISM: Artificial
<220> FEATURE:
<223> OTHER INFORMATION: Primer

<400> SEQUENCE: 32
gcgaattcca ccatggccgg acctgagctg gagatgcct                             39

<210> SEQ ID NO 33
<211> LENGTH: 39
<212> TYPE: DNA
<213> ORGANISM: Artificial
<220> FEATURE:
<223> OTHER INFORMATION: Primer

<400> SEQUENCE: 33
gcgaattcca ccatggccgg acctggcctg gtgagacct                             39
```

-continued

```
<210> SEQ ID NO 34
<211> LENGTH: 39
<212> TYPE: DNA
<213> ORGANISM: Artificial
<220> FEATURE:
<223> OTHER INFORMATION: Primer

<400> SEQUENCE: 34
gcgaattcca ccatggccgg gggaggctta gtgaagcct                                 39

<210> SEQ ID NO 35
<211> LENGTH: 39
<212> TYPE: DNA
<213> ORGANISM: Artificial
<220> FEATURE:
<223> OTHER INFORMATION: Primer

<400> SEQUENCE: 35
gcgaattcca ccatggccgg ggcagagctt gtgaagcca                                 39

<210> SEQ ID NO 36
<211> LENGTH: 39
<212> TYPE: DNA
<213> ORGANISM: Artificial
<220> FEATURE:
<223> OTHER INFORMATION: Primer

<400> SEQUENCE: 36
gcgaattcca ccatggccgg aggggcttg gtacagcct                                  39

<210> SEQ ID NO 37
<211> LENGTH: 39
<212> TYPE: DNA
<213> ORGANISM: Artificial
<220> FEATURE:
<223> OTHER INFORMATION: Primer

<400> SEQUENCE: 37
gcgaattcca ccatggccgg ggcagagctt gtgaggtca                                 39

<210> SEQ ID NO 38
<211> LENGTH: 69
<212> TYPE: DNA
<213> ORGANISM: Artificial
<220> FEATURE:
<223> OTHER INFORMATION: Primer

<400> SEQUENCE: 38
ggagccgccg ccgccgccag aaccaccacc accggatcca ccaccacccg aggaaacggt          60
gaccgtggt                                                                 69

<210> SEQ ID NO 39
<211> LENGTH: 69
<212> TYPE: DNA
<213> ORGANISM: Artificial
<220> FEATURE:
<223> OTHER INFORMATION: Primer

<400> SEQUENCE: 39
ggagccgccg ccgccgccag aaccaccacc accggatcca ccaccacccg aggagactgt          60
gagagtggt                                                                 69

<210> SEQ ID NO 40
<211> LENGTH: 69
```

```
<212> TYPE: DNA
<213> ORGANISM: Artificial
<220> FEATURE:
<223> OTHER INFORMATION: Primer

<400> SEQUENCE: 40
ggagccgccg ccgccgccag aaccaccacc accggatcca ccaccaccg cagagacagt     60 gaccagagt                                                            69

<210> SEQ ID NO 41
<211> LENGTH: 69
<212> TYPE: DNA
<213> ORGANISM: Artificial
<220> FEATURE:
<223> OTHER INFORMATION: Primer

<400> SEQUENCE: 41
ggagccgccg ccgccgccag aaccaccacc accggatcca ccaccaccg aggagacggt     60 gactgaggt                                                            69

<210> SEQ ID NO 42
<211> LENGTH: 69
<212> TYPE: DNA
<213> ORGANISM: Artificial
<220> FEATURE:
<223> OTHER INFORMATION: Primer

<400> SEQUENCE: 42
ggagccgccg ccgccgccag aaccaccacc accggatcca ccaccaccg atggggctgt     60 tgttttggc                                                            69

<210> SEQ ID NO 43
<211> LENGTH: 69
<212> TYPE: DNA
<213> ORGANISM: Artificial
<220> FEATURE:
<223> OTHER INFORMATION: Primer

<400> SEQUENCE: 43
ggagccgccg ccgccgccag aaccaccacc accggatcca ccaccactg atggggtgt      60 tgttttggc                                                            69

<210> SEQ ID NO 44
<211> LENGTH: 69
<212> TYPE: DNA
<213> ORGANISM: Artificial
<220> FEATURE:
<223> OTHER INFORMATION: Primer

<400> SEQUENCE: 44
ggagccgccg ccgccgccag aaccaccacc accggatcca ccaccaccg atggggctgt     60 tgttttggc                                                            69

<210> SEQ ID NO 45
<211> LENGTH: 69
<212> TYPE: DNA
<213> ORGANISM: Artificial
<220> FEATURE:
<223> OTHER INFORMATION: Primer

<400> SEQUENCE: 45
ggagccgccg ccgccgccag aaccaccacc accggatcca ccaccaccg atggggctgt     60
``` tgttttggc                                                            69

<210> SEQ ID NO 46
<211> LENGTH: 69
<212> TYPE: DNA
<213> ORGANISM: Artificial
<220> FEATURE:
<223> OTHER INFORMATION: Primer

<400> SEQUENCE: 46
ggagccgccg ccgccgccag aaccaccacc accggatcca ccaccaccg atggggctgt     60 tgttttggc                                                            69

<210> SEQ ID NO 47
<211> LENGTH: 69
<212> TYPE: DNA
<213> ORGANISM: Artificial
<220> FEATURE:
<223> OTHER INFORMATION: Primer

<400> SEQUENCE: 47
ggagccgccg ccgccgccag aaccaccacc accggatcca ccaccaccg atggggctgt     60 tgttttggc                                                            69

<210> SEQ ID NO 48
<211> LENGTH: 69
<212> TYPE: DNA
<213> ORGANISM: Artificial
<220> FEATURE:
<223> OTHER INFORMATION: Primer

<400> SEQUENCE: 48
ggagccgccg ccgccgccag aaccaccacc accggatcca ccaccaccag atggggggtgt   60 cgttttggc                                                            69

<210> SEQ ID NO 49
<211> LENGTH: 69
<212> TYPE: DNA
<213> ORGANISM: Artificial
<220> FEATURE:
<223> OTHER INFORMATION: Primer

<400> SEQUENCE: 49
ggagccgccg ccgccgccag aaccaccacc accggatcca ccaccaccg atggggctgt     60 tgttttggc                                                            69

<210> SEQ ID NO 50
<211> LENGTH: 50
<212> TYPE: DNA
<213> ORGANISM: Artificial
<220> FEATURE:
<223> OTHER INFORMATION: Primer

<400> SEQUENCE: 50
ggcggcggcg gctccggtgg tggtggatcc gcaatcatgt ctgcatctcc                50

<210> SEQ ID NO 51
<211> LENGTH: 51
<212> TYPE: DNA
<213> ORGANISM: Artificial
<220> FEATURE:
<223> OTHER INFORMATION: Primer

<400> SEQUENCE: 51

```
ggcggcggcg gctccggtgg tgtggatcc gcctccctat ctgtatctgt g         51
```

<210> SEQ ID NO 52
<211> LENGTH: 51
<212> TYPE: DNA
<213> ORGANISM: Artificial
<220> FEATURE:
<223> OTHER INFORMATION: Primer

<400> SEQUENCE: 52

```
ggcggcggcg gctccggtgg tgtggatcc gcctccctat ctgcatctgt g         51
```

<210> SEQ ID NO 53
<211> LENGTH: 51
<212> TYPE: DNA
<213> ORGANISM: Artificial
<220> FEATURE:
<223> OTHER INFORMATION: Primer

<400> SEQUENCE: 53

```
ggcggcggcg gctccggtgg tgtggatcc ctcactttgt cggttaccat t         51
```

<210> SEQ ID NO 54
<211> LENGTH: 51
<212> TYPE: DNA
<213> ORGANISM: Artificial
<220> FEATURE:
<223> OTHER INFORMATION: Primer

<400> SEQUENCE: 54

```
ggcggcggcg gctccggtgg tgtggatcc tcagcctctt tctccctggg a         51
```

<210> SEQ ID NO 55
<211> LENGTH: 51
<212> TYPE: DNA
<213> ORGANISM: Artificial
<220> FEATURE:
<223> OTHER INFORMATION: Primer

<400> SEQUENCE: 55

```
ggcggcggcg gctccggtgg tgtggatcc tcctccctga gtgtgtcagc a         51
```

<210> SEQ ID NO 56
<211> LENGTH: 51
<212> TYPE: DNA
<213> ORGANISM: Artificial
<220> FEATURE:
<223> OTHER INFORMATION: Primer

<400> SEQUENCE: 56

```
ggcggcggcg gctccggtgg tgtggatcc ctctccctgc ctgtcagtct t         51
```

<210> SEQ ID NO 57
<211> LENGTH: 51
<212> TYPE: DNA
<213> ORGANISM: Artificial
<220> FEATURE:
<223> OTHER INFORMATION: Primer

<400> SEQUENCE: 57

```
ggcggcggcg gctccggtgg tgtggatcc ctctccctgc ctgtcagtct t         51
```

<210> SEQ ID NO 58
<211> LENGTH: 32
<212> TYPE: DNA

```
<213> ORGANISM: Artificial
<220> FEATURE:
<223> OTHER INFORMATION: Primer

<400> SEQUENCE: 58
agtgcggccg catcagcccg ttttatttcc aa                                32

<210> SEQ ID NO 59
<211> LENGTH: 48
<212> TYPE: DNA
<213> ORGANISM: Artificial
<220> FEATURE:
<223> OTHER INFORMATION: Primer

<400> SEQUENCE: 59
ctatagaagg gtaatacgac tcactatagg gcgaattcca ccatggcc               48
```